United States Patent [19]

Havira

[11] 4,255,798
[45] Mar. 10, 1981

[54] METHOD AND APPARATUS FOR ACOUSTICALLY INVESTIGATING A CASING AND CEMENT BOND IN A BOREHOLE

[75] Inventor: R. Mark Havira, New Fairfield, Conn.

[73] Assignee: Schlumberger Technology Corp., New York, N.Y.

[21] Appl. No.: 911,016

[22] Filed: May 30, 1978

Related U.S. Application Data

[63] Continuation-in-part of Ser. No. 814,588, Jul. 11, 1977, abandoned.

[51] Int. Cl.³ .................................................. G01V 1/40
[52] U.S. Cl. ...................................... 367/35; 367/32; 181/105
[58] Field of Search .............................. 181/102, 105; 340/15.5 BH, 15.5 A, 15.5 AP, 15.5 AC; 367/25, 28–32, 35

[56] References Cited

U.S. PATENT DOCUMENTS

| | | | |
|---|---|---|---|
| 2,538,114 | 1/1951 | Mason . | |
| 2,825,044 | 2/1958 | Peterson | 340/18 |
| 2,848,891 | 8/1958 | Hunter, Jr. et al. . | |
| 3,175,639 | 3/1965 | Liben | 340/15.5 A |
| 3,265,151 | 8/1966 | Anderson | 340/15.5 BH |
| 3,295,628 | 1/1967 | Summers | 340/15.5 A |
| 3,340,953 | 9/1967 | Zemanek, Jr. | 340/15.5 BH |
| 3,401,772 | 9/1968 | Kokesh | 340/15.5 A |
| 3,401,773 | 9/1968 | Synnot | 340/15.5 A |
| 3,504,759 | 4/1970 | Cubberly, Jr. | 181/104 |
| 3,521,154 | 7/1970 | Maricelli | 367/25 |
| 3,595,069 | 7/1971 | Fowler | 73/67.2 |
| 3,697,937 | 10/1972 | Ingram | 340/15.5 A |
| 3,729,705 | 4/1973 | Grijalva | 340/15.5 BH |
| 3,732,947 | 5/1973 | Moran | 340/15.5 BH |
| 3,741,334 | 6/1973 | Kaule | 73/67.9 |
| 3,747,702 | 7/1973 | Beil | 340/15.5 AC |
| 3,794,976 | 2/1974 | Mickler | 367/28 |
| 3,883,841 | 5/1975 | Norel | 340/15.5 BH |
| 3,909,775 | 9/1975 | Lavigne | 340/15.5 BH |
| 3,914,987 | 10/1975 | Bickel et al. | 73/67.2 |
| 4,003,244 | 1/1977 | O'Brien et al. | 73/67.8 R |

FOREIGN PATENT DOCUMENTS 1499130  1/1978  United Kingdom .
405095   5/1974  U.S.S.R. .

OTHER PUBLICATIONS

"A Sonic Method for Analyzing the Quality of Cementation of Borehole Casings," Grosmangin et al., *Journal of Petroleum Technology*, Feb. 1961, pp. 165–171.

"Cement Bond Log-A Study of Cement and Casing Variables," Pardue et al., Journal of Petroleum Technology.

*Primary Examiner*—Howard A. Birmiel
*Attorney, Agent, or Firm*—Louis H. Reens; Kenneth Olsen

[57] ABSTRACT

Methods and apparatuses for acoustically investigating a casing in a borehole to derive the quality of a cement bond behind the casing and casing thickness are described. The techniques employ an acoustic pulse source having a frequency spectrum selected to stimulate a selected radial segment of the casing into a thickness resonance. The selected frequency spectrum enhances the reverberations between the inner and outer walls of the casing which traps the thickness reverberations with significant amplitudes for a duration depending upon the amount of acoustic energy leaked into adjacent media. The acoustic pulse causes acoustic returns which are formed by the reflections from interfaces between media of different acoustic impedances and acoustic energy leaked into the bore of the casing from the acoustic thickness reverberations stimulated within the casing walls. The acoustic returns are detected to generate a reflection signal which is processed to determine casing thickness or to evaluate the cement bond. The acoustic pulse has a frequency spectrum which is particularly effective in discriminating different cement bond conditions caused by small cement separations known as micro-annuli, around the casing. Several signal processing techniques and tools are described to provide accurate and high resolution cement bond evaluation and casing thickness determination by processing a portion of the reflection signal representative of the thickness reverberations.

70 Claims, 23 Drawing Figures

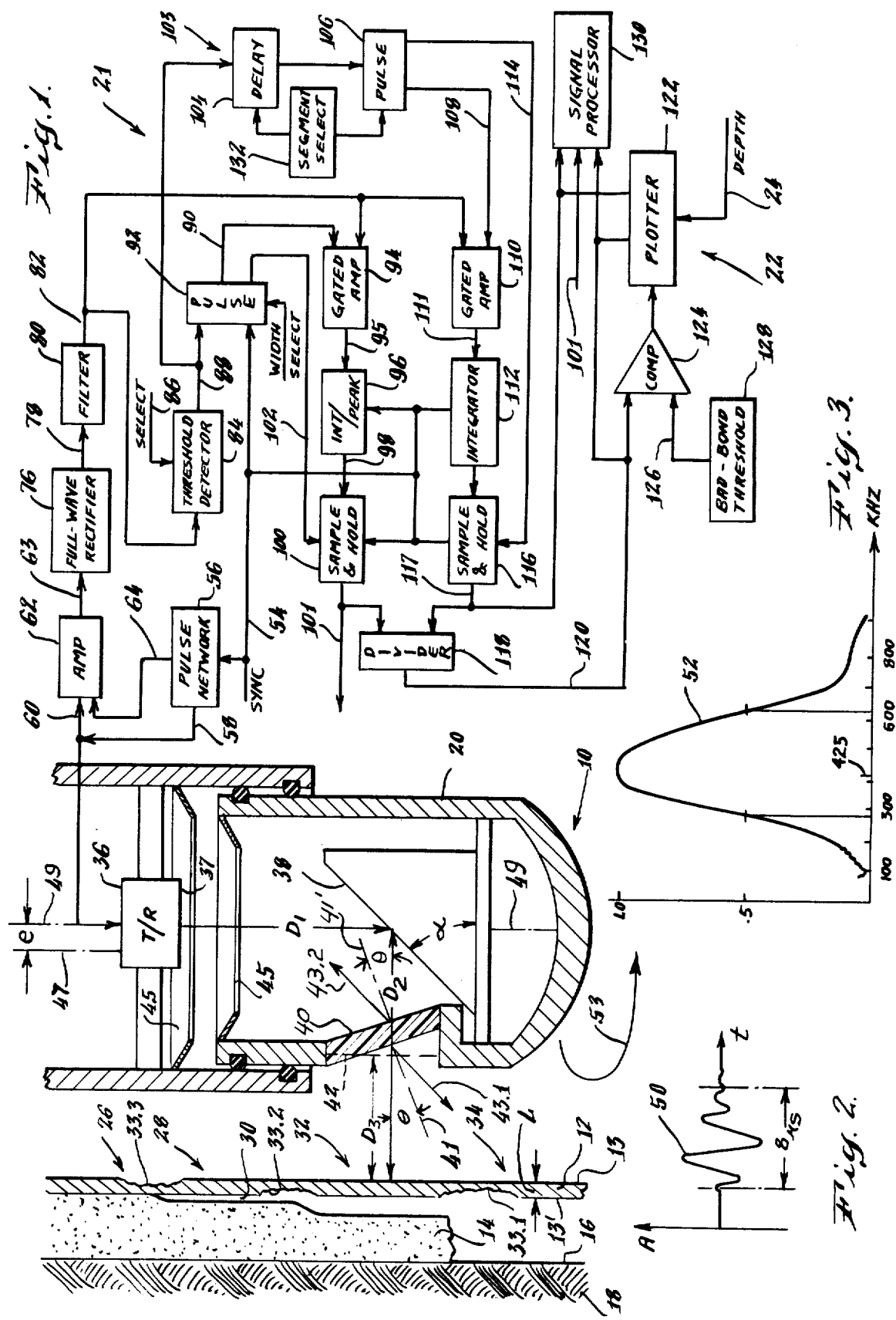

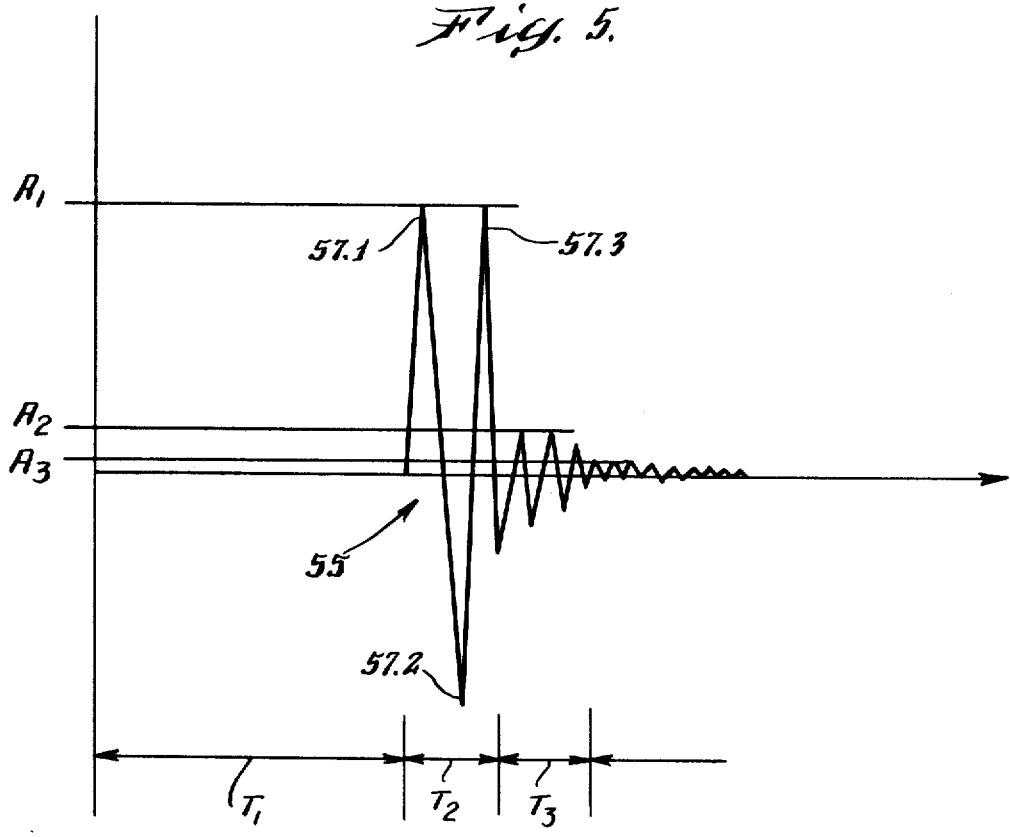

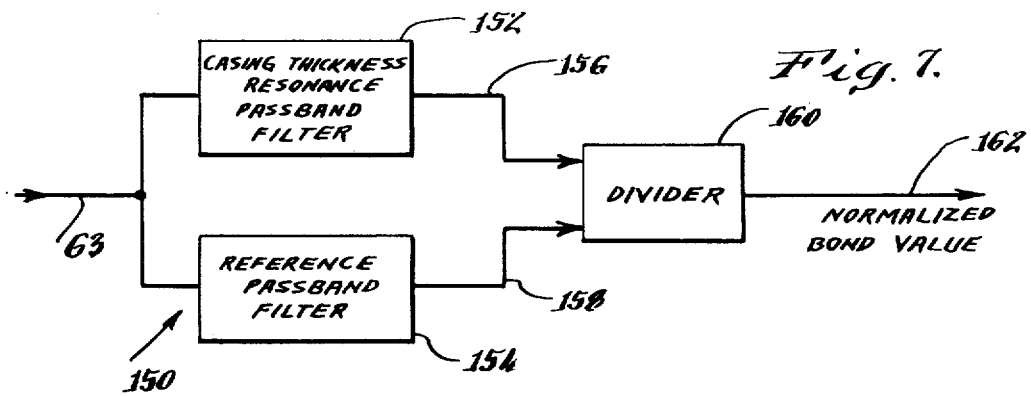
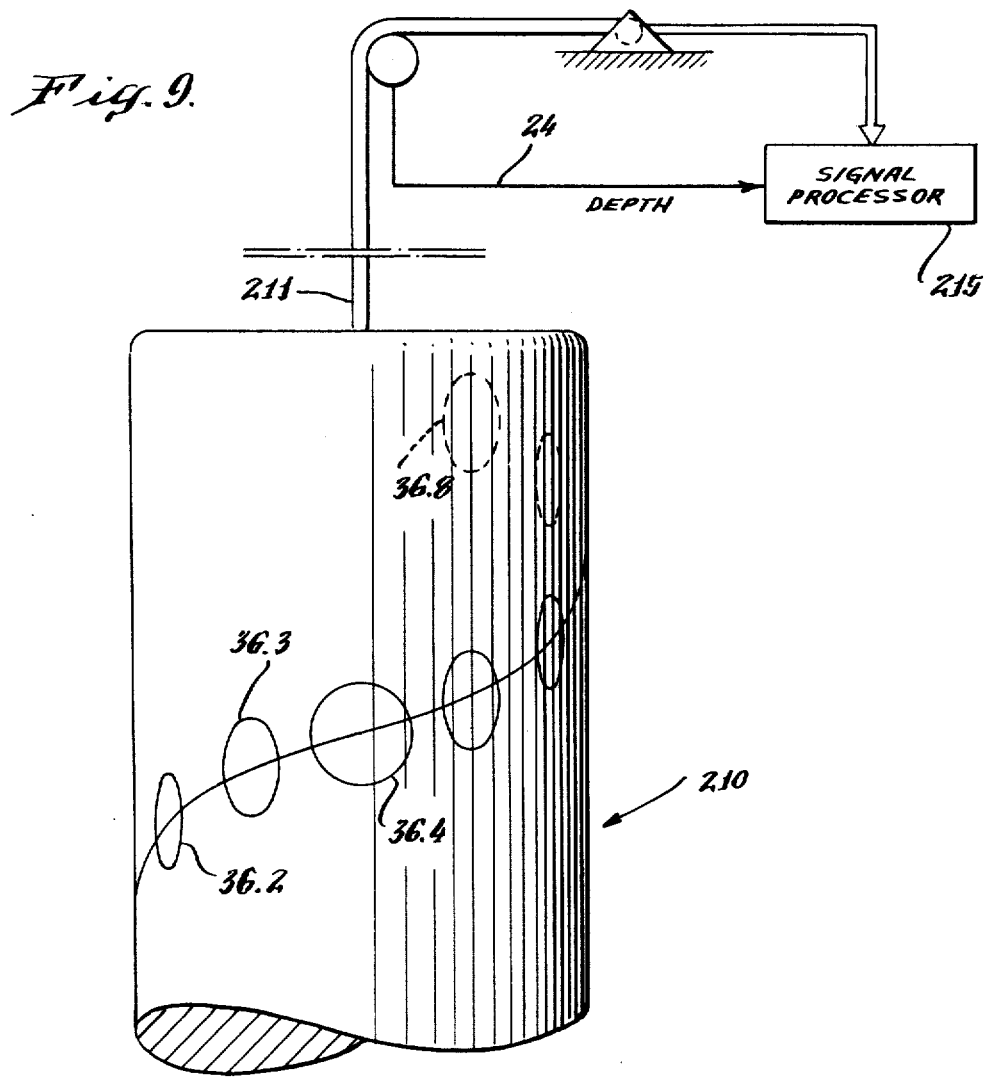

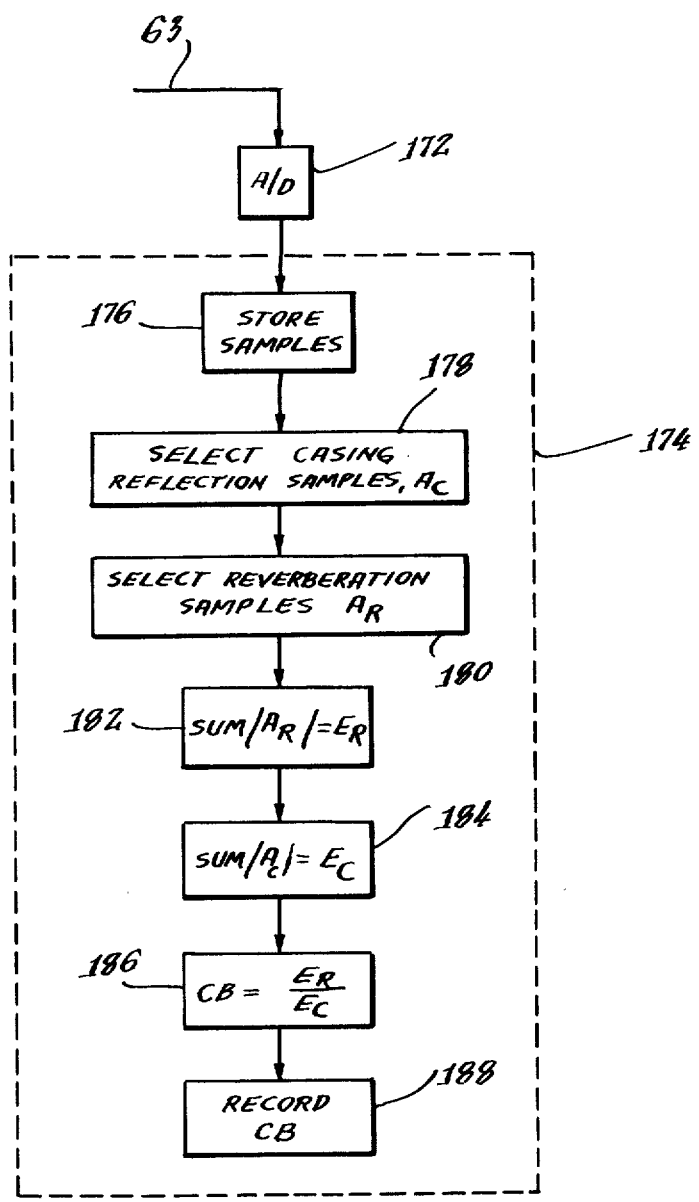

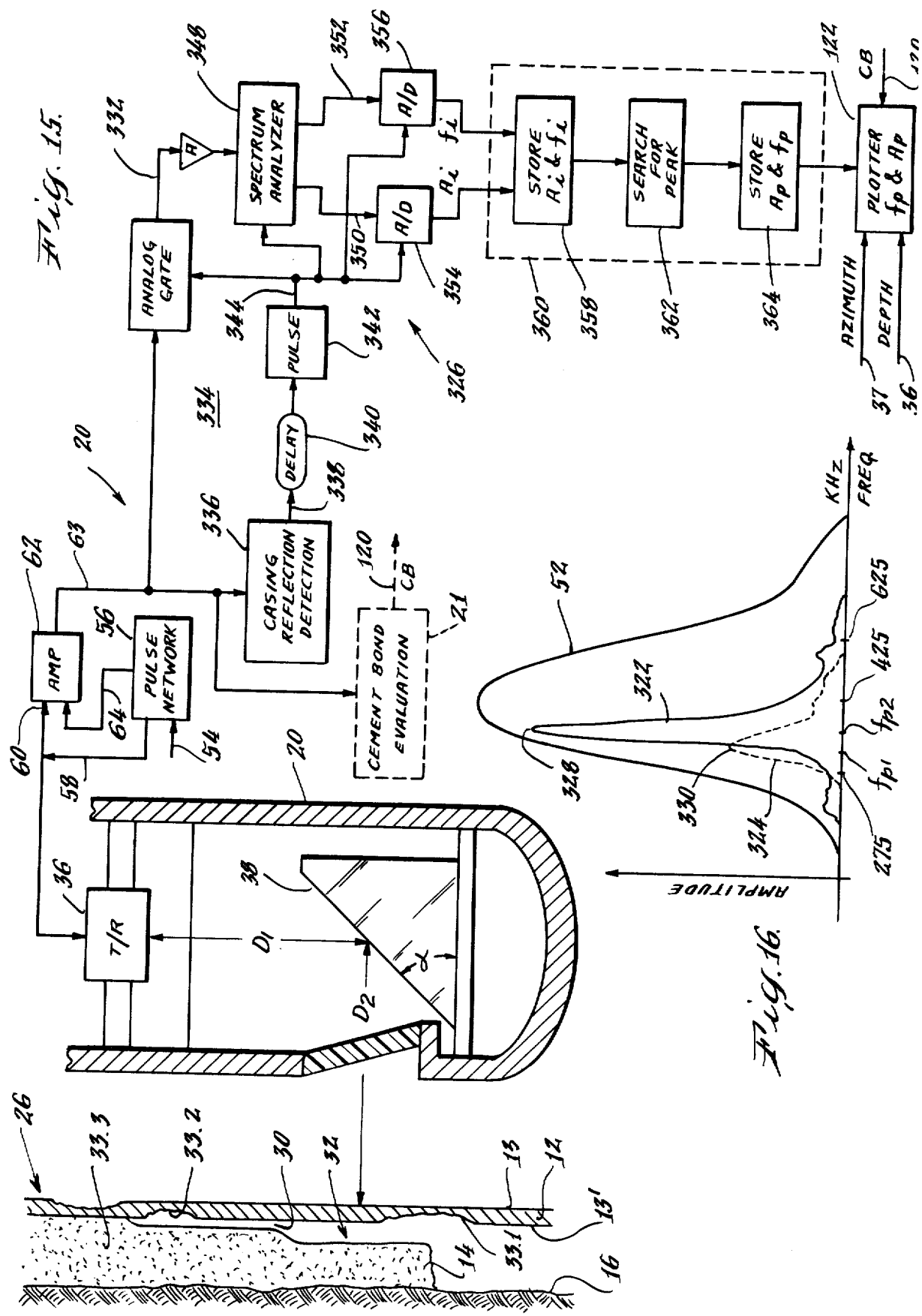

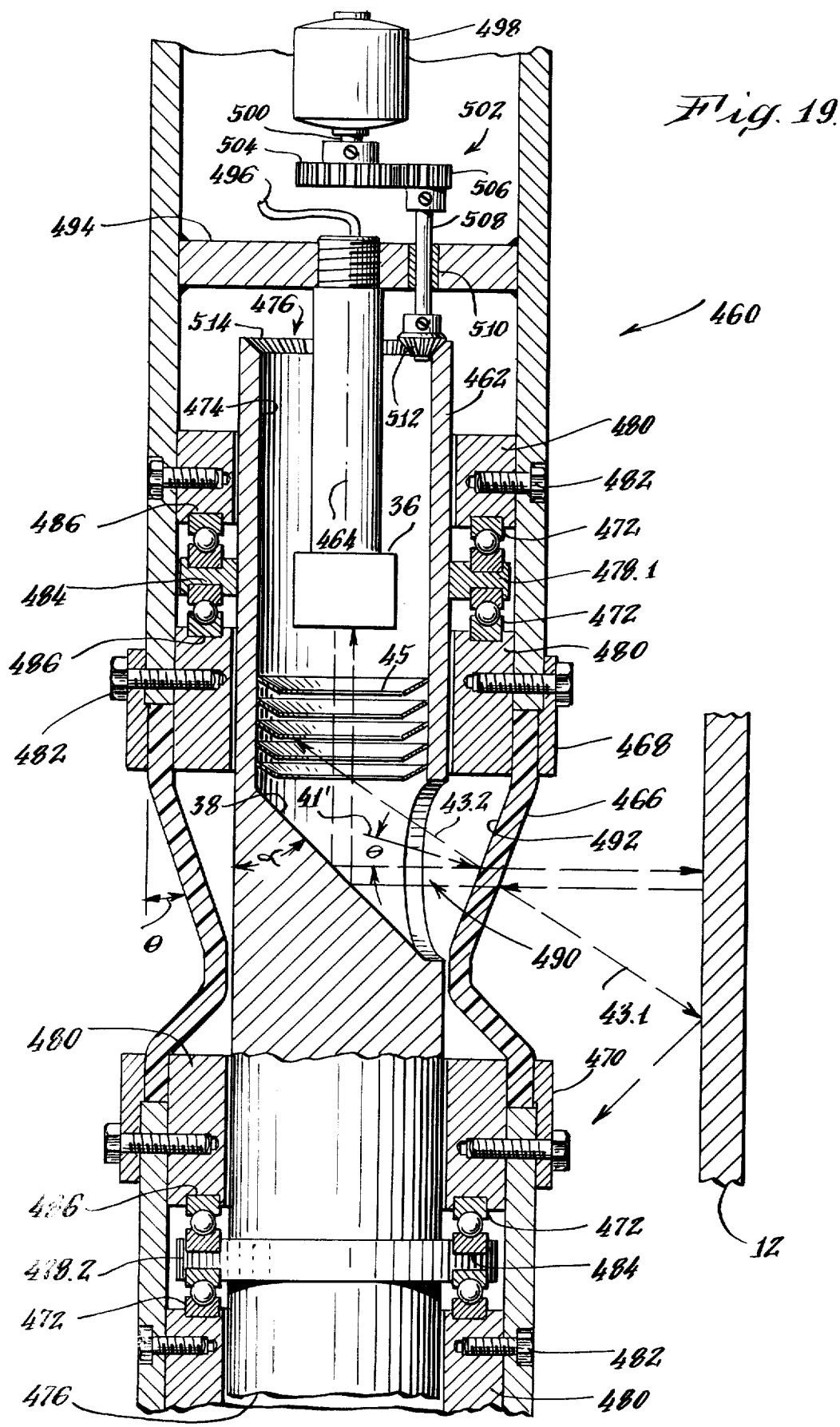

METHOD AND APPARATUS FOR ACOUSTICALLY INVESTIGATING A CASING AND CEMENT BOND IN A BOREHOLE

RELATED APPLICATION

This application is a continuation-inpart of pending application filed by Mark R. Havira on July 11, 1977 with Ser. No. 814,588, now abandoned entitled Method and Apparatus For Investigating The Quality of Cement Bond by Investigating Acoustic Pulse Echoes and assigned to the same assignee as of the present invention.

FIELD OF THE INVENTION

This invention relates to methods and apparatuses for acoustically investigating a borehole. More specifically, this invention relates to a method and apparatus using an acoustic pulse echo technique for investigating the qulaity of the cement bond to a casing and the thickness of the casing located in a borehole.

BACKGROUND OF THE INVENTION

In a well completion, a string of casing or pipe is set in a well bore and cement is forced into the annulus between the casing and the well bore, primarily to separate oil and gas producing horizons from each other and from water-bearing strata.

If the cement fails to provide a separation of one zone from another, then fluids under pressure from one zone may be able to migrate and contaminate an otherwise productive nearby zone. Migration of water in particular produces undesirable water cutting of a producing zone and possibly can make a well noncommercial.

Cement failures can occur in a variety of manners. For example, there may, for one reason or another, be a complete absence of cement behind the casing segment where the cement should be. This would be a gross cement bonding failure leading to rapid contamination between zones intended to be separated.

Another type of cement failure arises when the cement is present behind the casing, but a small cement-free annulus exists between the cement and casing. This annulus may be so thick as to enable hydraulic communication between zones leading to undesirable contamination.

Such annulus, however, may also be so thin as to effectively preserve the hydraulic security function of the cement. Such acceptable small annulus may arise from the technique employed to introduce the cement in the first place. For example, the cement typically is introduced under very high pressure such as produced by using a heavy mud to chase the cement plug down and into the annulus around the casing. The resulting pressure inside the casing causes a slight expansion of the casing and subsequent contraction when the heavy mud is removed. The magnitude of the contraction depends upon the pressure and casing thickness and tends to result in a slight separation, an annulus, between the cement and casing. It is important to know whether the cement is performing its function, i.e. whether the cement bond is hydraulically secure.

Techniques have been proposed to ascertain the quality of the cement bond. In this sense the term "bond" as used herein, is to be understood to include both those cases where the cement actually adheres to the casing as well as when there is no adhesion but instead a small micro-annulus which is so small as to prevent fluid communication between cement separated zones. In other words, the term "good bond" means that separation of zones by the cement is adequate to prevent fluid migration between the zones even in teh presence of a micro-annulus. It is, therefore, desirable that cement evaluation techniques identify such micro-annuli as good cement bonds while recognizing annuli incapable of separating zones as hydraulically insecure or bad bonds.

The problem of investigating the cement behind a thick casing wall with a tool located inside the casing has led to various cement evaluating techniques using acoustic energy.

For example, in the U.S. Pat. No. 3,401,773 to Synnott III a cement logging technique is described using a tool employing a conventional longitudinally space sonic transmitter and sonic reciever. The casing signal traveling through the casing is processed whereby a later portion, which is afftected by the presence or absence of cement, is extracted. The extracted segment is integrated to provide a measurement of its energy as an indication of the presence or absence of cement behing the casing. Although such technique provides useful information about cement defects behind the casing, the evaluation of the quality of the cement bond may not be sufficiently precise since the measurement averages cement conditions over a substantial distance between the transmitter and receiver and does not provide circumferential resolution i.e. information as to the bond condition at various points around the casing. Furthermore, the technique may characterize a hydraulically secure annulus as a defective cement bond because of inadequate energy transfer from the casing signal to the cement through the annulus.

A more precise technique for evaluating the cement condition is described in the U.S. Pat. No. 3,697,937 to Ingram and assigned to the same assignee as for this patent application. Ingram discloses a sonic transmitter-receiver with zero spacing to measure reflection coefficients from reflections produced by material discontinuities. Cement conditions in cased boreholes are evaluated by comparing the relative amplitude and phase of reflected sonic energy impinging upon paired acoustic transducers at a plurality of frequencies. The sonic investigation is described as particularly useful at sonic frequencies in the range from about 5 KHz to 50 KHz. At such sonic frequencies the reflection coefficients (the ratio of amplitudes of incoming waves to outgoing waves in the mud inside the casing) vary as a function of whether there is a cemented or uncemented annulus, the width of the annulus and hardness of the formation.

In the U.S. Pat. No. 3,732,947 to Moran et al an acoustic pulse technique for cement evaluation logging is described wherein the attenuation of acoustic signals reflected from material discontinuities is measured at radially resonant frequencies effectively without circumferential resolution. The measured attenuation constants are then employed to compute the thickness of the annulus and the cement with the computation dependent upon the type of formation as well as upon measurements conducted at different resonant frequencies. This technique employs low frequnecies where compensation for formation characteristics to be obtained from another well log are required. Furthermore, information on the thickness of the cement annulus is needed to derive an evaluation of the annulus between the cement and casing.

When acoustic cement evaluation techniques are carried out at low frequencies such as described in the patents to Ingram and Moran et al, so-called radial or hoop-mode resonances are observed. One resonance includes the casing-annulus system, a second higher resonance occurs for the cement annulus itself. The technique of employing such resonances to sense absence or presence of cement in the annulus around the casing does not lend itself easily to evaluating the cement bond quality in the presence of small casing-cement annuli.

In the U.S. Pat. No. 3,175,639 to Liben, an acoustic pulse echo technique is described to investigate the formation zone alongside a borehole. An acoustic pulse generator operating at a frequency of the order of about 10 MHz is applied adjacent the wall of a borehole and actuated to generate very short acoustic pulses towards the formation. The elapsed time between the transmitted sonic pulse generation and the reflected pulses are measured as well as the amplitude of the returned pulse. The measurements are then used to derive the acoustic impedance of the formation.

In the Liben patent a processing apparatus is described with which the return pulse occurring after the transmitted pulse is rectified and integrated. The integrated signal is indicated as proportional to the average amplitude of the return pulse. The integrated signal is used to derive the acoustic impedance of the formation alongside the borehole with the use of a measurement of the thickness of the mud cake, a knowledge of the amplitude of the transmitter pulse, the absorption characteristic of the mud and the acoustic impedance of the mud cake.

The acoustic pulse echo technique described in Liben does not lend itself well for evaluating the quality of the cement bond. The proposed frequency of operation by Liben is too high, thereby tending to characterize all micro-annuli as poor cement bonds. Furthermor, the acoustic transducer is mounted close to the borehole wall so that secondary transmission interference problems may occur such as when a returned echo is reflected from the transducer as a second transmission back to the formation.

In the U.S. Pat. No. 3,340,953 to Zemanek, an acoustic through-casing formation borehole logging technique is described with acoustic frequencies determined by the casing thickness. The apparatus functions by transmitting acoustic energy from a transmitter to a pair of remotely spaced receivers. The frequency of the acoustic energy is selected on the basis of a particular relationship depending upon the velocity of the shear wave in the casing, an arbitrary dimensionless number and the casing thickness. The suggested transmitter frequencies are from 300 KHz to 460 KHZ for a casing thickness of ¼ inch thickness and correspondingly lower frequencies for thicker casings.

The Zemanek system does not operate on a specific isolated casing segment but, because of the transmitter-receiver spacing along the borehole, provides an average evaluation over the spacing involved. Zemanek neither describes an apparatus nor a method for investigating the cement bond by analyzing the relections from radially successive interfaces.

The U.S. Pat. No. 3,883,841 to Norel et al describes a similar acoustic pulse echo technique as in Liben for measuring the acoustic impedance of material alongside a wall in a borehole. The acoustic pulse transducer in Norel is provided with different acoustic coupling layers between the flush mounted transducer and the borehole. The Norel et al device suggests employing a source pulse whose frequency spectrum occurs in the range from about 100 KHz to about 5 MHz. This is a frequency range of generally the same bandwidth as proposed in U.S. Pat. No. 2,825,044 to Peterson who suggested an ultrasonic device for exploration of a borehole wall with acoustic waves at frequencies from 100 KHz to 10 MHz.

The acoustic echoes obtained as proposed by Norel et al are stated as useful for checking the cement bond. Norel teaches that to measure the acoustic impedance of the material in contact with the casing, two consecutive peaks of received impulses are to be extracted and their ratio generated for use in a computation network to derive the acoustic impedance. Since a casing thickness may vary in practice as much as from 10% to 20%, the Norel gating approach to extract successive reflection is difficult to implement. Furthermore, the acoustic impedance coupling layers suggested by Norel introduce attentuation. As a result, the potential error in measuring individual reflections is increased, thus reducing the effectiveness of Norel et al's analysis of the acoustic investigation.

In a simplified approach described with reference to FIG. 15, Norel et al propose to check the cement bond by directly integrating the entire received echo signal and recording the resulting integration as a function of depth. This technique includes the strong casing reflection whose inclusion obscures the more significant later reflections and is likely to include formation echoes in well-bonded hard formations.

A frequency range such as proposed by Norel et al includes at the low end frequencies tending to drive the casing-annulus into hoop-mode resonance with the attendant sensitivities which make cement bond evaluations in the presence of small annuli difficult. At the high end of Norel et al's frequency range, the casing-cement annuli are likely to be consistently interpreted as bad cement bonds even though the cement might be hydraulically secure. Furthermore, the spacing between Norel's transducer feeler and the casing tend to appear as a small annulus, thus obscuring the evaluation of the cement bond.

When an acoustid pulse echo technique for investigating a borehole is employed, it is desirable to obtain an adequate number of cycles in the reflected pulses before a secondary interference as herein described with respect to Liben is obseved. When an acoustic pulse transducer as described in Norel et al is mounted flush to the inner wll of a casing, the first echo return occurs very soon and its reflection from the transducer back to the casing causes secondary reflections which tend to interfere with the initial echo signals of interest.

One can introduce special acoustic coupling layers between the transducer and the casing as proposed by Norel et al. With such layers, however, the echo signals tend to be also reduced in amplitude. Furthermore, the proximity of the transducer to the material interfaces reduces the number of echo signals with useful amplitudes before secondary transmission interference arises. Though use of high frequencies such as from one to five MHz enable sharper or shorter duration transmitter pulses, those same frequencies tend to be incompatible for evaluating small casing-cement annuli. Such high frequency sonic waves also tend to be affected by the casing surface whose roughness may cause destructive interference.

When an acoustic pulse producer such as described in Norel et al is employed in an ultrasonic echo testing device as described in Russian Patent No. 405095 or the U.S. Pat. No. 3,974,476 to Cowles, the increased spacing suggested by the latter between the transducer and the casing enables reception of a greater number of cycles. However, in such case the intermediate layers proposed by Norel et al between the transducer and the casing tend to severely attenuate the echo signals which already arrive with reduced amplitude by virtue of the increased spacing.

The U.S. Pat. No. 3,339,666 to McDonald describes an acoustic pulse echo technique for a cased borehole using an acoustic frequency at which the casing appears transparent. The suggested acoustic pulse frequency range is about 100 KHz, with a particular range suggested between 200 to 400 KHz. The reflections are transmitted from the borehole tool to the surface where all of the reflections occurring after a gating time of about 100 microseconds following the firing and before the next succeeding acoustic pulse from the transmitter are rectified, integrated and recorded.

McDonald characterizes the reflection segment selected for integration and recording as representative of the acoustic impedance of the formation. In practice, however, significant reflections from the formation at the casing thickness resonance frequency occur in limited situations such as when the cement is well bonded to both the casing and the formation and when the formation itself can provide a strong reflection. Formation reflections tend to be cluttered by secondary transmission effects, such as when an initial acoustic reflection from the inner wall of the casing causes a secondary transmission when partially reflected off the face of the transducer.

When the borehole wall is rough or has craters or crevasses, as frequently occurs, the formation acoustic reflections tend to be scattered and quite weak by the time they arrive at the acoustic transducer. When the cement annulus is not properly bonded to the casing and formation, further attenuation and scattering of the formation reflection is likely, resulting in further weakening or complete loss of the formation reflection.

McDonald further proposes the transmission of the reflection through suitable conductors in a cable. Techniques for the transmission of high frequency signals of the order of 500 KHz such as occur in the reflection signal are well known. Well logging cables, however, are typically limited to signals whose frquencies occur below about 100 KHz. As a result, a high frequency reflection signal attributable to reverberations between the inner and outer casing walls would be highly attenuated by the cable.

It is important in well logging operations to obtain information as to the current condition of the casing employed in boreholes. The installed casing may be exposed to various corrosions due to chemically active corrosive solutions, electrolytic corrosion due to ground currents or contact between dissimilar metals. Corrosion of the outside casing wall may result in a highly undesirable hydraulic communication between formation zones which must remain isolated from each other by the cement. Excessive wear may arise due to abrasion from fluid flows. Hence, over a period of time, the borehole casing may deteriorate with excessively thin and weakened resions. Such deterioration can be harmful causing collapse of the protective casing and perhaps loss of the well or, if leaks develop in the casing, uncontrolled movement of fluids within the well and adjacent formations. Unlike well tubing, once casing is installed in a well, it is difficult or impossible to remove the casing for inspection. It is, therefore, particularly useful to be able to inspect the casing in situ to determine the presence and location of bad casing conditions.

Ultrasonic pulse echo techniques for determining the thickness of materials have been extensively proposed in the art. Commencing, for example, with the U.S. Pat. No. 2,538,114 to W. P. Mason, an apparatus is described for measuring the thickness of a material by noting its resonance frequency when the material is irradiated with ultrasonic energy. In the U.S. Pat. No. 2,848,891 to J. E. Hunter et al, a technique is described whereby the grain size of materials is measured by observing the ultrasonic frequency response of the material. In the U.S. Pat. No. 3,595,069 to Fowler et al a system is disclosed whereby an ultrasonic sensor is stimulated into a resonance and the resonance frequency measured to detemine the value of the parameter for which the sensor is used. In the U.S. Pat No. 4,003,244 to O'Brien et al, the thickness of a material is measured by employing a pulse echo technique.

Various frequency domain techniques have been employed in acoustic investigations to determine the thickness of materials. For example, in an article entitled "Ultrasonic Signal Processing Concepts for Measuring the Thickness of Thin Layers", published at page 249 of the December, 1974 issue of Materials Evaluation by J. L. Rose and P. A. Meyer, a frequency analysis is described for determining the thickness of a thin layer. As described in this article, an input acoustic pulse is applied with sufficient bandwidth to cover the fundamental or harmonic resonance frequency of a thin layer placed between two materials. A spectral profile of the echoes from various layers is made as illustrated in FIGS. 11 and 12 of this article. With particular reference to the broadband frequency spectra shown in FIG. 12, dips in the frequency spectrum occur at those frequencies which bear a particular relationship to the thickness of the material being measured. The center frequency of such dips, however, are not conveniently measured, particularly when the frequency spectrum of an echo reveals several dips.

Acoustic techniques have been described with which a plate, whose thickness is to be measured, is driven into a thickness resonance by utilizing a feedback of resonating vibrations. One such technique is described in U.S. Pat. No. 3,741,334 which issued to W. Kaule.

Kaule describes a particular ultrasonic technique for determining the thickness of a plate by measuring its thickness resonance. Resonance is induced in the plate by first subjecting the plate to a noise source for a first interval and recording the decaying free resonance ultrasonic sound during a second subsequent interval. After the plate has ceased resonating, the previously stored sound is played back and used to induce resonant vibrations in the plate followed by a subsequent recording of the decaying sound after the second inducement. This process is repeated to achieve a high amplitude resonance in the plate and enable a measurement of the plate's resonance frequency and thus the plate's thickness. Frequency is measured by counting the amplitude peaks of the decaying resonating vibrations over a particular interval or by determining the time needed to count a particular number of peaks.

An alleged improvement over the Kaule U.S. Pat. No. 3,741,334 is described in U.S. Pat. No. 3,914,987 to Bickel et al. The improvement appears to relate to use of a bidirectional counter and a delay, but determination of the resonance frequency still involves the counting of individual peaks in the decaying vibrations from the resonating plate.

When an acoustic pulse echo technique is used to determine the thickness of a casing cemented in a borehole penetrating an earth formation, the acoustic returns have a complex form. A waveform representative of such acoustic return is illustrated in FIG. 4 herein and shows that a reliable peak to peak frequency determination is at best difficult and more likely impractical. Furthermore, the casing bore is circular tending to produce acoustic interferences from reflections of surface irregularities and the like; thus further cluttering acoustic returns.

In addition, the time available for the investigation of the thickness of any one small casing segment is limited if an extensive investigation of the casing is to be completed within a resonable time. Hence, the time needed to execute an acoustic feedback investigation of the type described in the Kaul and Bickel et al patents does not in practice appear tolerable.

In an article entitled "Broad-Band Transducers, Radiation Field and Selected Applications" by E. P. Papadakis and K. A. Fowler and published at page 729 of Vol. 50 Number 3 (Part 1) of the 1971 issue of *The Journal of the Acoustical Society of America*, a pulse induced resonance technique is described for determining the thickness of a thin material. The technique describes a selective time-domain gating of pulses reflected by the thin material and an analysis of their frequency content with a spectrum analyzer. An automatic tehcnique for deriving the thickness of the thin material is not described.

SUMMARY OF THE INVENTION

In an acoustic pulse echo technique for investigating the casing in a borehole in accordance with the invention, an acoustic pulse is directed at a selected radial segment of the casing. The acoustic pulse has a frequency spectrum selected to stimulate the selected segment into a thickness resonance whereby an enhanced entrapment of reverberations between the inner and outer casing walls is obtained. Acoustic returns caused by acoustic reflections and leakage from the reverberations are detected to produce a reflection signal from which both an evaluation of the quality of the casing-cement bond and the casing thickness can be derived.

The acoustic waves at the casing thickness resonance have been found to be effectively insensitive to hydralically secure micro-annuli provided the wavelengths employed exceed the thickness of such micro-annulus by a sufficient amount. The spacing between the receiver-transducer and the casing inner wall is so selected that an adequate number of cycles of acoustic returns are received before secondary transmission interferences arises.

As described with reference to a preferred signal processing embodiment, the strong casing reflection signal from the inside wall of the casing is separated from the reflection signal and a subsequent reverberation segment of the reflection signal selected as indicative of the energy of the echo produced by the casing-cement interface. The selected reverberation segment is rectified and integrated to generate a bond signal indicative of the quality of the cement bond.

In order to remove the effect of tool-tilts and borehole mud anomalies, the previously separated casing reflection signal is employed to normalize the bond signal. One described method for this involves a measurement of the peak of the casing reflection signal and effectively dividing the signal representative of the energy in the selected reverberation segment by the measure amplitude of the casing peak to arrive at a normalized bond signal.

The derived bond signal may be plotted as a function of borehole depth or compared with a signal representative of desired bond quality to identify those borehole regions where the cement bond is hydraulically inadequate.

A cement bond signal derived in accordance with the invention varies with casing thickness changes. As described with reference to one technique in accordance with the invention, the cement bond signal is normalized with a signal representative of the casing thickness to substantially remove the effect of casing thickness variations.

With a technique for deriving the cement bond evaluation behind a radial segment of the casing, the casing thickness can also be advantageously obtained so that a precise estimate of the casing-cement interface can be made at such location, while also being sensitive to such local casing deteriorations caused by corrosion or wear.

With the pulse echo technique for evaluating the cement bond in accordance with the invention, the ability to discriminate between good and bad cement bonds is significantly enhanced. A relatively sharp discrimination between casing-cement annuli which are hydraulically secure and insecure is obtained independent of formation type.

It is, therefore, an object of the invention to provide an acoustic pulse echo borehole investigation method and apparatus for evaluating the quality of the cement bond. It is a further object of the invention to enhance the sensitivity of an acoustic pulse echo technique for the evaluation of the quality of the bond between the casing and cement. It is still further an object of the invention to evaluate the quality of the cement bond to the casing with good circumferential resolution.

With an acoustic pulse echo technique in accordance with the invention, the selected reverberations segment may be further advantageously used to provide an indication of the casing thickness As described with reference to one technique, the selected reverberation segment is analyzed to determine the frequency of components which contribute to a desired peak in the frequency domain of the reverberation segment. The frequency of this peak is used to determine the thickness of the casing.

With a technique for determining the casing thickness in accordance with the invention, a reliable casing thickness determination is obtained substantially free from interference due to casing surface irregularities, signal noise and borehole conditions and is particularly useful to determine large variations in casing thickness. Advantageously, the technique can determine variations in thickness along the circumference of the casing such that a thin section at one circumferential point will not be overlooked or cancelled out by integration with offsetting thick sections as with some prior art devices.

One technique for deriving the frequency components in the reverberation segment of the reflection signal may employ a spectrum analyzer. The output from the spectrum analyzer is recorded in a memory such as a magnetic disc or a solid state device. The recorded spectrum analysis of the reverberation segment is thereupon replayed and scanned by a peak detector to detect when a desired peak in the spectrum occurs. Detection of the desired peak causes activation of a sample and hold network which stores a signal repesentative of the frequency at which the peak occurs as an indication of the thickness of the casing. With a casing thickness detection technique in accordance with the invention, a reliable determination of casing thickness can be obtained effectively free from interference due to borehole environmental factors and casing conditions such as surface irregularities.

It is, therefore, an object of the invention to provide an acoustic pulse echo technique for deriving an indication of the thickness of a casing installed in a borehole.

As described with reference to several embodiments for investigating the casing, a tool is used having either an acoustic source, which is rotated as the tool is moved along a cased borehole, or which has a plurality of circumferentially distributed acoustic sources. With such tool discrete radial casing segments can be inspected with good circumferential resolution. If desired, a precise location of flaws in the casing thickness or cement bond can be obtained by providing azimuth tool orientation information.

The term radial segment as used herein means the segment of the casing extending between its walls and surrounding a given radius which extends generally normal to the casing wall from the center of the casing.

In accordance with still another acoustic pulse echo technique for investigating a casing in accordance with the invention, the reflection signal is digitized downhole by a high speed analog to digital converter. The digitized reflection signal may then be processed with a tool mounted processor, but preferably the digitized reflection signal is transmitted at a suitable pulse rate to a surface located signal processor. The signal processor is programmed to derive an evaluation of the quality of the cement bond and the thickness of the casing from the digitized reflection signal.

With acoustic pulse echo investigation and signal processing techniques in accordance with the invention, a reliable evaluation of the quality of the cement bond and the casing thickness is obtained with a single pass of the same investigating tool.

It is, therefore, a further object of the invention to provide an acoustic pulse echo investigation technique with which both the quality of the cement bond and the casing thickness can be determined.

These and other advantages and objects of the invention can be understood from the following description of several embodiments described in detail in conjunction with the drawings.

BRIEF DESCRIPTION OF DRAWINGS

FIG. 1 is a schematic representation of one apparatus for evaluating the quality of the cement bond and/or the thickness of the casing in accordance with the invention;

FIG. 2 is a waveform representation of a preferred acoustic pulse generated in the apparatus shown in FIG. 1;

FIG. 3 is a plot of the frequency spectrum of the acoustic pulse shown in FIG. 2;

FIG. 5 is an amplitude response curve useful in specifying the performance requirement of a transducer preferred for use in an acoustic borehole investigation in accordance with the invention;

FIG. 7 is a block diagram of a signal processing apparatus for evaluating the cement bond in accordance with the invention;

FIG. 8 is a block diagram of another form for a signal processing apparatus for evaluating the cement bond in accordance with the invention;

FIG. 9 is a schematic representation of another cement bond evaluation tool in accordance with the invention;

FIG. 15 is a schematic representation of an apparatus for determining the thickness of a casing in accordance with the invention;

FIG. 16 is an amplitude frequency plot of several spectra obtained with the apparatus of FIG. 15;

FIG. 18 is a block diagram of part of an apparatus for detecting casing thickness in accordance with the invention.

DETAILED DESCRIPTION OF EMBODIMENTS

Figure 4A:
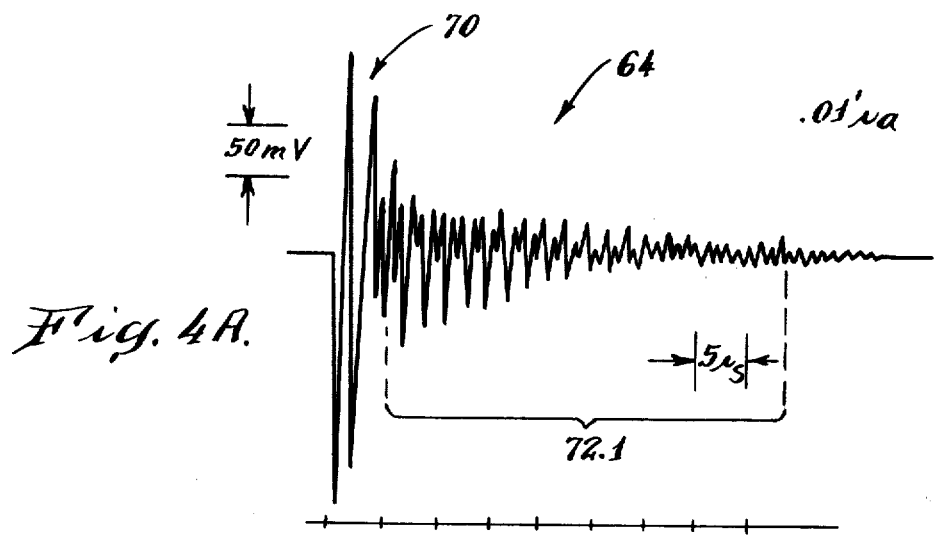
FIGS. 4A, 4B and 4C are illustrative waveforms representative of acoustic reflections obtained in a pulse-echo investigation technique conducted in accordance with the invention.

FIGS. 1, 2, 3, 4 and 5

With reference to FIGS. 1 through 3, a system 10 is illustrated for acoustically investigating the quality of the cement bond between a casing 12 and an annulus of cement 14 in a borehole 16 formed in an earth formation 18. An acoustic pulse producing tool 20 is suspended inside the casing 12 with a cable (not shown) having signal paths along which signals for control of tool 20 and for its observations are transmitted between a signal processor 21 in tool 20 and surface located controls and signal processing equipment such as shown at 22. A depth signal, representative of the depth in borehole 14 of tool 20, is derived on a line 24 with a conventional depth monitor (not shown) coupled to the cable with which the tool 20 is moved along casing 12.

The cylindrical casing 12 is shown in partial section as well as the surrounding cement annulus 14. The shape of the borehole 16 is shown as uniform and the casing correspondingly illustrated as equidistantly spaced from the borehole wall. In practice, however, the borehole wall is likely to be irregular with crevasses and cracks. Hence, the cement annulus 14 may vary in thickness and the spacing between the casing 12 and the formation 18 may vary.

The cement 14 is shown with various bond states frequently encountered. At region 26 the cement is shown as adhering to the casing 12 while at 28 a microannulus, μa, 30, which is hydraulically secure, occurs. In the region 32 the annulus 30 is shown enlarged to a thickness with which vertical zone separation is no longer obtainable while at region 34 the cement is entirely absent. The cement-free regions at 28, 32 and 34 normally are filled with water or a combination of water and mud. These cement conditions do not necessarily occur as illustrated and are shown here for purposes of illustrating the invention. Suffice it to note that the cement conditions at regions 26 and 30 are to be evaluated as good bonds while those at regions 32 and 34 must be detected as bad.

Casing 12 is further shown with externally corroded segments 33.1, 33.2 and an internally corroded segment 33.3 where the casing wall has been reduced in thickness. Such corrosions may occur at other regions and can be particularly harmful when one occurs in a region leading to hydraulic communication between zones which must remain isolated from each other. The illustrated corroded segments 33.1-33.3 may appear as actual gaps or occur as scaly segments which present a rough surface appearance and may even partially separate from the good parent metal. The scaly segments become saturated by the borehole fluid segments so that acoustic investigation of the good parent metal beneath the scaly segments can still be made.

The tool 20 fits within the casing 12 which normally is filled with water or a mixture of water and mud. The tool 20 is kept central in the casing 12 with appropriate centralizers (not shown) as are well known in the art. In the practice of the invention the tool 20 preferably is kept parallel to the casing wall, though the tool may be displaced relative to the central axis of the casing 12. As will be further explained with reference to FIG. 1, some compensation for tilt conditions, i.e. when the tool 20 forms an angle with the casing axis, is obtained with the system 10.

Tool 20 is further provided with a transducer 36 functioning as a pulse transmitter and receiver. In some instances the transmitter and receiver functions can be produced by separate devices. The transducer 36 is oriented to direct an acoustic pulse onto an acoustic reflector 38 and then through a window 40 onto a selected radial segment of the casing 12. The acoustic pulse is partially passed through casing 12 and partially trapped in casing 12 with reverberations occurring in the radial segment at the thickness resonance of the casing.

The nature of the window 40 may vary and preferably is formed of such material and so inclined relative to the direction of travel of the acoustic pulses from transmitter 36 that the acoustic returns can pass through with a minimum of attenuation and source of reflections. Window 40 can be made of polyurethane such as sold by the Emerson-Cummings Company as CPC-41 having an acoustic velocity of about 1,700 meters/second and a density of about 1.1 grams/cm$^3$. Such material exhibits a similar acoustic impedance as a fluid placed in the space between source 36, reflector 38 and window 40 to equalize pressure across window 40.

The fluid with which the space inside the tool between the transducer 36, and window 40 is filled is preferably selected for low or minimum attenuation and an acoustic impedance which will not contrast too widely from that of the borehole fluid in the frequency range of interest. An acceptable fluid may, for example, be ethylene glycol.

Window 40 is inclined at an angle $\theta$ which is defined as the angle between the direction of propagation of the initial acoustic pulse from transducer 36 and the normal 41 to the window surface area upon which this acoustic pulse is incident. Such inclination serves to deflect secondary transmissions such as 43.1 in a direction which avoids window produced interference. Suitable annular acoustic absorbing surfaces such as baffles 45 may be used inside the tool to trap and absorb acoustic reflections 43.2 from the inside wall of window 40. The size of the angle $\theta$ may be of the order of 20° to 30" as suggested in the U.S. Pat. No. 3,504,758 to Dueker.

Although the inclination of window 40 could be in a direction measured relative to the incident beam travel path, as shown in the U.S. Pat. Nos. 3,504,758 to Dueker, or 3,504,759 to Cubberly, the preferred orientation is as illustrated in FIG. 1 herein to enable use of a larger reflector 38.

The size of reflector 38 is significant in that the reflector surface area influences focusing of the acoustic energy onto the casing 12 and the capture of a sufficient acoustic return for improved signal to noise ratio.

If the reflectors of Dueker or Cubberly are enlarged, the internal reflections from their windows are likely to be intercepted by the reflectors and redirected onto the receiver transducer in interference with the desired acoustic returns from the casing. When a window inclination as illustrated in FIG. 1 herein is employed, however, a large reflector 38 can be used, with effective dimensions sufficient to either focus or preserve the beam shape of the acoustic energy directed onto casing 12 and provide a significant acoustic return to receiver transducer 36.

The inclination of window 40 can be clearly distinguished from that employed in Dueker or Cubberly with reference to the orientation of the internal window normal 41' relative to the point of incidence of the acoustic beam along its travel path $D_2$ from reflector 38. When as shown in FIG. 1, the normal 41' lies between the beam travel path $D_2$ and the acoustic receiver function of transducer 36, the inclination angle and also the angle of incidence, can be considered as positive. This angle would also be positive when the internal normal lies between the beam travel path and a separate acoustic receiver such as employed in the acoustic borehole apparatus illustrated in the previously identified Russian Patent SU No. 405,095.

In case of a window orientation as shown in the Dueker or Cubberly patents, the inclination angle or angle of incidence can be construed as negative because the internal window normal is on the other side of the acoustic beam travel path and points away from the receiver transducer.

With the window inclination as illustrated in FIG. 1, care should be taken to avoid directing reflections such as 43.2 onto the transducer 36; the inclination angle, therefore, should be positive and sufficiently large, but not so large as to cause significant diffraction effects. The inclination angle should also not be so large that reflections such as 43.2 fail to be either absorbed or intercepted by baffles 45.

A portion of the acoustic pulse is passed through casing 12 and, in turn, is partially reflected by the next interface, which in region 26 would be cement material, while at the regions 28, 32 would be the annulus 30 and water-mud at region 34.

In the embodiment of FIG. 1 the acoustic transducer 36 is selectively located so that its effective spacing (the travel time for an acoustic pulse) to the casing 12 is sufficiently long to permit isolation of interference from secondary transmission caused when the strong acoustic casing reflection is again partially reflected by either a window or the transducer 36 back to casing 12 to produce new reverberations and secondary acoustic returns. A desired total spacing D is obtained by locating the transducer 36 generally at an axial distance $D_1$ from reflector 38, which in turn is spaced a distance $D_2$ from the casing 12.

The total distance $D=D_1+D_2$ between transducer 36 and casing 12 is further selected sufficiently long so that the desired acoustic returns including those attributable to reverberations trapped between the casing inner and outer walls 13 and 13' respectively can be detected. The total distance D, is thus sufficiently long to include those acoustic returns prior to their decay to some small value as a result of leakage into adjoining media. On the other hand, the total spacing D is kept sufficiently small to avoid undue attenuation by the mud external to tool 20 and the fluid inside tool 20.

In addition to these spacing considerations, the distance $D_1$ between transducer 36 and reflector 38 has been found to affect the sensitivity of the system to tool positions away from a concentric relationship with the central axis 47 of casing 12. It should be understood that tool 20 is provided with suitable centralizers, not shown, as are generally well known. Despite the presence of such centralizers some tool displacement, shown as an eccentricity distance e between the casing axis 43 and tool axis 49, may arise from a number of conditions inside casing 12. The distance $D_1$, for this reason is selected to tolerate a maximum amount of tool eccentricity e.

The optimum value for the spacing $D_1$ depends further upon such factors as the effective dimensions of surface 37 of transducer 36 such as its diameter in case of a disk transducer 36.

For a disk transducer having a diameter of the order of about one inch to produce a pulse such as 50 in FIG. 2 with a frequency spectrum such as 52 in FIG. 3, the total distance $D_1$ is generally of the order between about 2 to about 3 inches.

A basis for selecting the total distance D is thus to assure sufficient time to receive all those acoustic returns which significantly contribute to an accurate judgment as to the quality of the cement bond in the presence of a small casing-cement annulus. The total distance D should be long enough to enable the portion in the acoustic returns attributable to a bad cement bond to be received free from interference.

The acoustic returns include acoustic reflections arising as a result of the interaction of the initial acoustic pulse with various media. A first acoustic casing reflection arises from the interface between the water or mud inside the casing 12 and the inside casing wall 13. This first reflection tends to be consistently the same, varying with mud consistency, inside casing wall condition, and tilts of tool 20. Subsequent acoustic returns arise as a function of reflections from successive media as well as the leakage of acoustic reverberations entrapped inside the casing.

Thus, after the first casing reflection, the acoustic portion transferred into casing 12 is now reverberating inside the casing walls 13-13' and leaking energy at each reflection. The energy lost depends upon the coefficients of reflections $r_o$ (the reflection coefficient between the fluid inside casing 12 and the casing) and $r_1$ (the reflection coefficient between casing 12 and the next layer which may be cement as in region 26 or water as in region 32). The duration over which significant reverberations last inside the casing walls 13-13' is a function of the casing thickness. Since casing of greater thickness tend to cause longer lasting reverberations, the total spacing D between the casing and receiver-transducer should be correspondingly increased.

When a window, which is normal to the direction of travel of the acoustic pulse, as suggested in dotted line at 42 in FIG. 1 is employed, the casing reflection and other acoustic returns produce reflections at the interface between window 42 and the mud inside casing 12. Such reflections appear as secondary transmissions which are returned to the casing to produce a second casing reflection with subsequent reverberations in the casing and thus also secondary acoustic returns. These secondary acoustic returns disturb the cement evaluation, particularly in case of a good cement bond when the formation also has a smooth surface. In this latter situation reflections caused by secondary reverberations mix with a significant reflection from the formation, giving an overall erroneous impression of a bad bond.

Hence, another criterion for determining an acceptable casing to receiver distance may involve selecting a distance $D_3$, between a window 42 and casing 12, such that secondary acoustic returns decay below a preselected percentage of their initial value. Thus, it can be shown that the number $N_r$, of reverberations in the steel casing 12 in such range is given by the relationship $$N_r = \frac{\ln(x)}{\ln(|r_o r_1|)}$$

where x is the percentage fraction.

The distance $D_3$ can then be shown as given by the relationship $$D_3 > N_r L \, (C_o/C_1)$$

where L is the thickness of the casing 12, $C_o$ the velocity of sound of the material inside the casing, mainly water, and $C_1$ the velocity of sound in the casing, namely steel.

As a numerical example to arrive at an acceptable total casing to receiver distance, one may assume the values for the materials employed in the following Table 1.

TABLE 1

| | Acoustic Impedance | Density | Velocity of Sound |
|---|---|---|---|
| | Z in g/cm²sec | ρ in g/cm³ | C in ft/sec |
| water | $Z_0 = 1.5 \times 10^5$ | $\rho > 1$ | $C_0 = 4920$ |
| steel | $Z_1 = 4.6 \times 10^6$ | $\rho_1 = 7.8$ | $C_1 = 19,416$ |
| cement | $Z_2 = 7.7 \times 10^5$ | $\rho_2 = 1.96$ | $C_2 = 12,000$ | and $Z_2 = Z_0$ in case of a bad bond.

Using these constants the values for the reflection coefficients can be determined as $r_o = 0.937$ $r_{1G} = -0.731$ (for a good bond)

$r_{1B} = -0.937$ (for a bad bond).

The casing to receiver distance or $D_3$ can be determined from the above constants and time setting constraints. For example, if the reverberations in the casing are to decay to about five percent of their initial value, the distance $D_3$ can be from about one and one-quarter inch to about three inches for a normally occurring range of casing thicknesses L from about 0.2" to about 0.65". By relaxing the final value of decay of the casing reverberations the source to casing distance can be decreased, though about one inch is likely to be a lowest possible limit for $D_3$. Since the largest casing thickness is preferably accommodated, the distance from the transducer 36 to either window 40 or 42 is chosen such that there is no secondary transmission interference over the time interval of interest. The distance $D_3$, when applicable, is chosen such that secondary reflections attributable to the window do not present signal interference. When the tool 20 employs a window such as 40, secondary reflections from such window are no longer a consideration in selecting the transducer to casing spacings.

In the selection of the transducer 36, a disk transducer having a diameter to wavelength ratio of greater than unity is employed. In practice, a disk transducer having a diameter of about one inch has been found useful. The transmitter pulse is formed of such duration and frequency as to stimulate a selected radial segment of the casing upon which the pulse is incident into a thickness resonance. Acoustic energy is transferred into the casing and reverberates in an enhanced manner with the duration and magnitude of reverberations highly sensitive to the layer of material adjacent the external surface of casing 12. Such sensitivity, however, should not include hydraulically secure micro-annuli such as at region 28.

In the selection of the frequency spectrum of the acoustic pulse from transducer 36, a primary basis is determined by the fundamental thickness resonance frequency of casing 12. Such resonance enables a trap mode with which enhanced acoustic energy is trapped in the casing. The subsequent reduction of trapped energy in the casing may be considered the result of leakage attributable to the degree of acoustic coupling to adjacent media. The frequency spectrum of the acoustic pulse should preferably include either the fundamental or a higher harmonic thereof. Expressed in mathematical terms, the stimulating frequency in the acoustic pulse is given by $$f_o = N(C_1/2L)$$

where $C_1$ is the casing compressional velocity and L is the casing thickness measured normal to the casing wall and N is a whole integer.

An upper limit of the frequency spectrum of the acoustic pulse is set by practical considerations such as casing roughness, grain size in the steel casing and mud attenuation. Furthermore, the hydraulically secure micro-annulus must appear transparent.

In practical cement bond applications a casing-cement annulus equal or smaller than 0.005" (0.127mm) represents a good cement bond and thus prevents hydraulic communications between zones intended to be separated. When annuli larger than this value occur, these should be construed as bad cement bonds. Furthermore, as long as an annulus is less in thickness than about 1/30 of a wavelength of an acoustic wave traveling in water, such annulus is effectively transparent to an acoustic wave of such wavelength. Hence, in terms of casing-cement annuli, the frequency spectrum of the acoustic pulse should be selected such that $$f_o < \frac{C_o}{(\mu a_t) \times 30}$$

where $C_o$ is the velocity of sound in water and $\mu a_t$ is the thickness of the annulus.

In practical terms, casing thicknesses L normally encountered are from about 0.2" (5.08 mm) to about 0.65" (16.51mm). Hence, with an effective frequency of from about 300 KHz to about 600 KHz for the acoustic pulse, the casing 12 can be stimulated into a trap mode which is insensitive to hydraulically secure micro-annuli. This frequency spectrum is selected so that the trap mode can be stimulated with either the fundamental frequency or its second harmonic for the thicker casings.

Within such frequency spectrum, the duration of the reverberations inside the steel casings become sensitive to both good and bad micro-annuli. For an acceptable micro-annulus the casing reverberations (and their observed leakage) decay more rapidly than for an excessively large micro-annulus.

The acoustic transmitter pulse is thus formed with characteristics as illustrated in FIGS. 2 and 3. The transmitter pulse 50 shown in FIG. 2 represents a highly damped acoustic pulse of a duration of the order of about eight microseconds. The frequency spectrum of such pulse 50 is shown in FIG. 3 with a frequency-amplitude curve 52 showing a 6 db (one-quarter power) bandwidth extending from about 275 KHz to about 625 KHz with a peak at about 425 KHz. The thick casings having a trap mode below 275 KHz are driven into resonance primarily with a higher harmonic such as the second which occurs with significant amplitude in the bandwidth of the spectrum 52.

The transmitter 36 can be formed of a variety of well known materials to produce pulse 50 with the frequency spectrum 52. For example, an electrical signal having these characteristics can be formed and amplified to drive a suitable piezoelectric transducer 36 capable of operating as a transmitter and receiver.

Preferably transducer 36 is formed with a piezoelectric disk crystal which is backed with a critically matched impedance such that an acoustic pulse is formed at the resonant frequency of the disk. The backing material has an impedance selected to match that of the crystal while strongly attenuating the acoustic pulse to avoid reflections from the back. In some applications a protective front layer may be employed integrally mounted on the front of the transducer 36. Such front layer is preferably made of a low attenuation material having an acoustic impedance which is approximately the geometric mean between the crystal impedance and the expected borehole fluid impedance. Such front layer has a quarter wavelength thickness as measured at the center resonant frequency of the crystal.

Since the disk is critically matched, the acoustic output pulse has a wide frequency bandwidth. Excitation of such transducer 36 may then be achieved with an electrical pulse of very short duration. For example, an impulse having a rise time of from about 10 to about 100 nanoseconds and a fall time of 0.5 to about 5 microseconds can be used.

In the transmitter mode transducer 36 may be actuated in a repetitive manner at a pulse rate, say, of the order of a hundred pulses per second. At such rate a circumferential region around casing 12 can be scanned as tool 20 is moved upward along the casing by making reflector 38 and its associated window 40 a rotatable mounting as illustrated for rotation in the direction of arrow 53.

FIG. 5 defines the performance criteria for a suitable transducer 36. The transducer has a center acoustic frequency at about 425 KHz with a 6 db bandwidth of 300 KHz. The FIG. 5 illustrates an acceptable received amplitude response curve 55 when transducer 36 is energized with a pulse drive signal of about two microsecond duration and directed at a water/air interface spaced from the transducer at a distance equivalent to about 100 microseconds of two-way acoustic wave travel time, $T_1$. The output signal from transducer 36 as a result of the echo from the interface preferably should have an appearance as illustrated where the first echo, formed of the three main peaks 57.1, 57.2 and 57.3, should be of no greater total duration, $T_2$, than approximately six microseconds. The level $A_2$ of the noise immediately after the first echo should be about 50 db below the level $A_1$ of the peaks 57 and have a duration $T_3$ of less than about 30 microseconds. The noise level $A_3$ following interval $T_3$ preferably should be at least 60 db below the level $A_1$ of peaks 57.

The controls and circuitry necessary for firing of the transducer may originate from above ground equipment or from a suitable clock source located in tool 20. In either case, recurring synch pulses are produced on a line 54 of FIG. 1 to activate a pulse network 56 which generates a suitable pulse on line 58 to drive transducer 36 while simultaneously protecting the input 60 to amplifier 62 with a signal line 64.

The transducer 36 responds to the pulse from network 56 with an acoustic pulse of the type as shown in FIGS. 2 and 3. The acoustic pulse is directed onto reflector 38 which acts to direct the acoustic energy at the wall of casing 12. The effect of reflector 38 aids in compensating for variations in alignments of the acoustic pulse out of the plane normal to the casing wall. The reflector 38 can be a flat surface at an angle α of about 45° to the acoustic energy from transducer 36 or a slightly concave or convex surface.

When the acoustic pulse 50 impinges upon casing 12, some of the energy is reflected and some transferred into the casing 12. The reflected energy is returned to transducer 36 via reflector 38 and is reproduced as an electrical signal and applied to input 60 of amplifier 62.

The energy transferred into casing 12 reverberates, causing in turn further acoustic returns to transducer 36. The resulting received output from transducer 36 may have the appearance as illustrated with reflection signal waveforms 64, 66 and 68 in FIGS. 4A, 4B and 4C.

The initial segment 70 of each reflection signal waveform represents the strong initial casing reflection whose duration is of the order of about five microseconds. The remainder 72 is characterized as a reverberation segment in that it represents a large number of cycles of pulses representative of acoustic reverberations whose magnitudes decay over a period of time. The decay period varies as a function of the type of cement bond, as can be observed for waveforms 64, 66, 68 obtained with respectively differently sized annuli 30 around casing 12.

Except for the initial casing reflection segment 70, the reflection signals 64, 66, 68 do not have a highly predictive pattern wherein the peaks are precisely defined and extractable. Accordingly a prior art technique such as shown in the previously identified U.S. patent to Norel et al for comparing adjacent peaks to ascertain decay time constants for the waveforms is difficult to implement.

Instead, the signal processing segment 21 of the apparatus 10 operates on each reflection signal by separating the reverberation segment 72 from the initial strong acoustic casing reflection segment 70 and subsequently integrating the reverberation segment 72 over a particular time span to determine the energy therein.

In the embodiment of FIG. 1, the reflection signals from transducer 36 are amplified in amplifier 62 whose output is applied to a full wave rectifier 76 to produce on line 78 a DC signal representative of the amplitude of the received acoustic wave. The DC signals are filtered in a filter 80 to provide on line 82 a signal representative of the envelope of the waveforms from transducer 36.

The envelope signal on line 82 is applied to a threshold detector 84 which initiates subsequent signal processing by detecting the start of the initial casing reflection segment 70 (see FIG. 4). The amplitude at which the threshold detector 84 operates can be varied with a selector control applied to line 86 and can be automatically set. The output on line 88 of threshold detector 84 is applied to activate an enabling pulse on output 90 from a pulse producing network 92. The pulse from this network 92 is selected of such duration that the envelope segment on line 82 and attributable to the initial casing reflection 70 is gated through an amplifier 94 as a casing reflection signal.

The duration of the enabling pulse on output 90 is selectable so that the entire casing reflection segment 70 can be selected in the event its duration varies. The DC form of the casing reflection signal is applied to an integrator network or peak amplitude detector 96 to produce a signal representative of the amplitude of the casing reflection 70 on line 98. This casing amplitude signal is stored such as with a sample and hold network 100 actuated by an appropriate pulse derived on line 102 from network 92 at the end of the pulse on line 90.

The output 88 from the threshold detector 84 is also applied to a reverberation segment selection network 103 including a delay 104 which produces an enabling pulse to pulse producing network 106 at a time after the initial casing reflection 70 has terminated. Network 106 generates a segment selection pulse on line 108 commencing at the beginning of the reverberation segment 72 and having a duration sufficient to gate the entire envelope form of the reverberation segment 72 (see FIG. 4) through gating amplifier 110 to integrator 112. The segment selection pulse on line 108 commences after the initial casing reflection and terminates after the desired number of acoustic returns of interest have been received but before secondary transmission interference arises. A typical pulse would start about six microseconds after the initial casing reflection is detected and would last for a period of about 40 microseconds after an acoustic pulse issued such as shown in FIGS. 2 and 3 and with a spacing D of the order of about three inches.

The integrator 112 integrates the envelope form for a time period determined by the pulse on line 108. At the end of this latter pulse a signal on line 114 from a pulse producer 106 activates a sample and hold network 116 to store a signal representative of the energy in the reverberation segment 72.

The outputs from sample and hold networks 100, 116 are applied to a combining network in the form of a divider 118 which forms a quotient by dividing the signal representative of the energy in the reverberation segment 72 by the normalizing signal indicative of the amplitude of the casing reflection 70 to generate a normalized energy bond signal on output line 120. The normalized energy signal on line 120 can be transmitted to above ground for recording reflection energy as a function of the depth on a plotter 122. The normalized energy signal may also be applied to a comparator 124 for comparison with a reference signal on line 126 derived from a network 128 and representative of the threshold level between good and bad cement bonds. The output 130 from comparator 124 indicates the presence or absence of a good cement bond can also be recorded on plotter 122 as a function of depth.

With the signal processing embodiments, the bond signal on line 120 is made less sensitive to tool tilts and attenuation in the fluid whereby the acoustic energy is directed at casing 12 along a plane which is skewed relative to the axis of the casing 12. When such condition occurs, the received acoustic returns are reduced in amplitude and may be interpreted as good cement bonds when, in fact, the cement bond may be bad. By employing the amplitude of the initial casing reflection as a gauge of tool tilt and mud conditions, the bond signal on line 120 provides a reliable indication of the cement bond quality.

There may in certain cases arise a need to obtain a bond signal which has not been normalized or which may be normalized at a later time. In such case the output 117 of the sample and hold network 116 is the bond signal which may be transmitted to above ground equipment for recording such as on a tape recorder or on plotter 122 or in the memory of a signal processor 130 after conversion to a digital form.

After a bond signal has been generated and a new synch pulse occurs on line 54, the synch pulse is applied to several reset inputs of sample and hold network 100, 116 and integrators 96, 112. The reset of the sample and hold networks 110, 116 can be delayed for a smoother output until such time as the outputs from integrators 96, 112 are ready for sampling.

The selection of a signal representative of the acoustic reverberation return 72 is obtained with a pulse produced on line 108 as can be determined with a segment selection network 132. This network controls the length of the delay 104 and the width of the enabling pulse from pulser 106. As previously described with reference to FIGS. 4A, 4B and 4C, the reverberation segment 72 is selected in such manner that the casing reflection 70 is effectively excluded.

This exclusion can be advantageously achieved by the signal processor 21 since it is activated by the detection of the strong casing reflection 70 as sensed by threshold detector 84. The resulting integration of the remaining envelope provides a sharp discrimination between a good bond signal and a bad bond signal. For example, the integration of the reverberation segment 72.1 of the waveforms 64 in FIG. 4A will be greater than the integration of the reverberation segment 72.3 of waveform 68 in FIG. 4C by a factor of about 3. When the area of the envelopes are compared for an example as set forth in Table 1, with the resulting reflection coefficients for $r_0$ and $r_1$ for good and bad cement bonds, an integration ratio of about 3.8-to-1 between bad and good signals occurs. Hence, an extremely sharp good-to-bad bond contrast is obtained which is likely to be obtained even in the presence of a dense mud inside the casing 12.

With certain types of cement one may wish to construe a micro-annulus of a thickness of the order of about 0.010 inches (0.25mm) as a good cement bond. In such case, the frequency spectrum 52 of the acoustic pulse 50 may be adjusted to investigate the cement. One may, for example, employ two types of acoustic pulses of different frequency spectrum, one having the fundamental frequency and the other acoustic pulse having a harmonic. If the results from these pulses do not give the same reading, a hydraulically secure micro-annulus can be concluded to be present.

Theoretically a bond will appear as good for a micro-annulus having a thickness of the order of half wavelength (about 0.08 inches). However, in practice such large annulus is unlikely to arise and other conventional cement quality investigation techniques can be employed to identify such unlikely large annulus as a poor cement bond.

FIGS. 6A–6C and 7

Figure 4B:
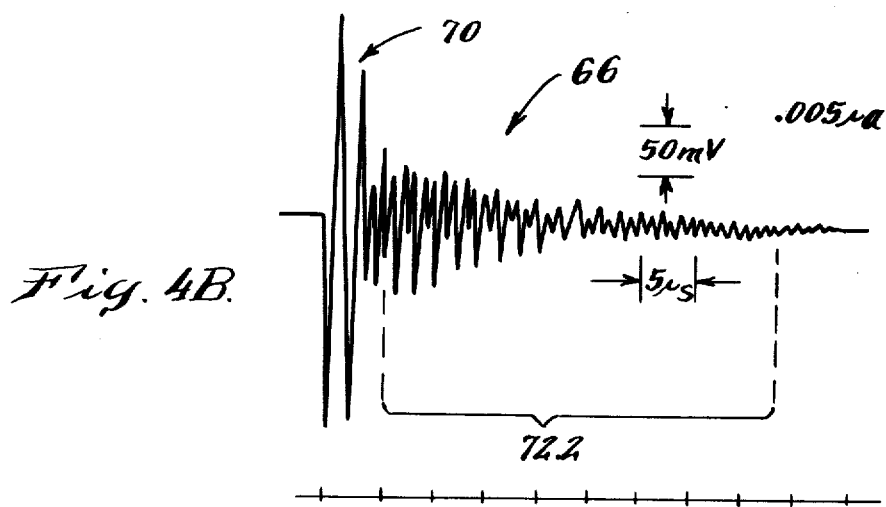
Figure 4C:
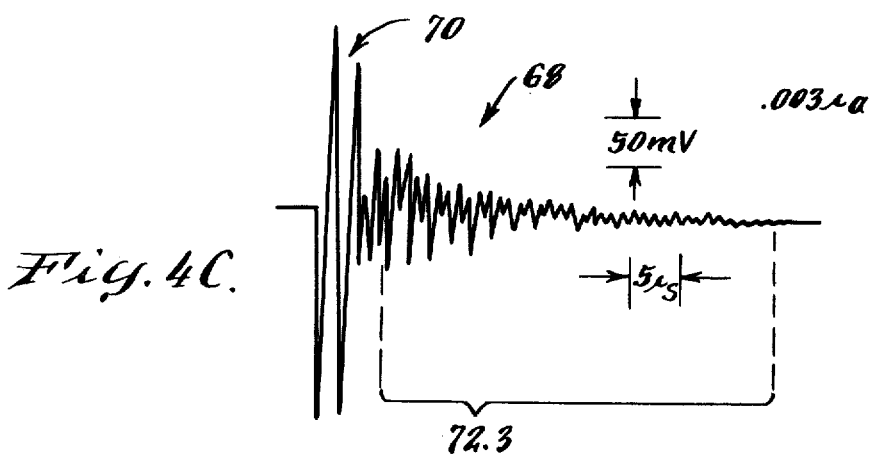
Figure 6A:
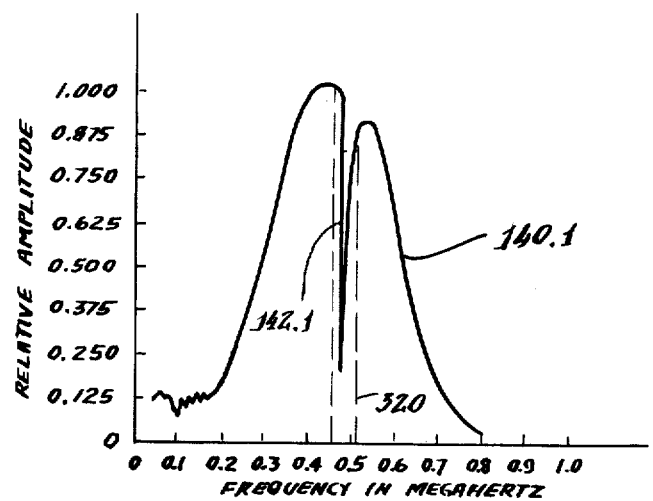
FIGS. 6A-6C are illustrative spectra of acoustic reflections observed with an acoustic investigation apparatus in accordance with the invention.
Figure 6B:
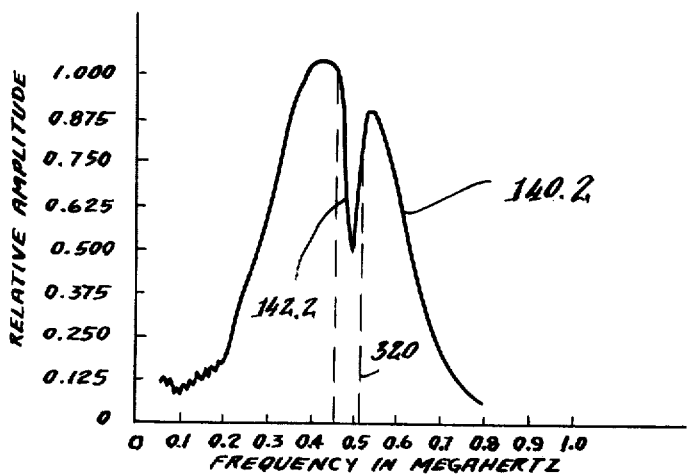
Figure 6C:
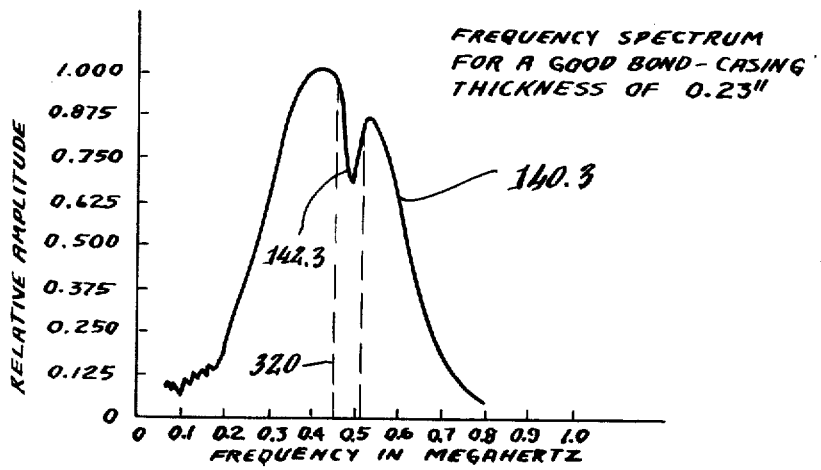

FIGS. 6A through 6C illustrate the effectiveness of tool 10 when a frequency spectrum is made on the observed entire acoustic returns such as illustrated in FIGS. 4A–4C. The spectra 140 of FIGS. 6A–6C represent respectively a bad bond with a large annulus, an intermediate bonding situation such as with an annulus of 0.005" and a good cement bond. The spectra 140 when originally obtained may have varied in absolute magnitude because the reflection changes in the tool eccentricity e and the coupling of acoustic energy to the cement 14 behind the casing 12 varies. Thus for a good cement bond, the absolute amplitude of the acoustic returns is lower than for a bad cement bond. The relative size of dips 142, however, varies with a larger dip for a bad cement bond and a smaller dip 142 for a good cement bond. For convenience, the spectra 140 are shown in FIGS. 6A–6C with generally equal amplitudes so that their dips 142 can be evaluated by a visual comparison with each other. The significance of dips 142 should be determined in light of the overall energy spectrum of the reflection signal.

The sharp digs 142 in spectra 140 are centered at the trap mode or thickness resonance of the casing from which the reflections came. In the spectra 140 the dips 142 occur at 0.5 MHz (500 KHz) for a 0.23 inch thick casing and resemble the effect of a narrow bandwidth energy trapping filter. In the case of a bad bond, such as for spectrum 140.1 in FIG. 6A, the dip 142.1 is deep, indicative that a relatively substantial amount of energy at the thickness resonance has been trapped inside the casing walls 13-13'.

The improvement of the cement bond is evidenced in spectrum 140.2 by a correspondingly smaller amount of energy being trapped inside the casing walls 13-13'. Hence, dip 142.2 in FIG. 6B is smaller in comparison with dip 142.1 in FIG. 6A while dip 142.3 in FIG. 6C is the smallest for a good cement bond.

FIG. 7 illustrates an embodiment 150 for evaluating the cement bond utilizing the sharpness of the dips 142 in spectra 140 of FIGS. 6A–6C. The output 63 of amplifier 62 in network 21 is applied to two passband filters 152 and 154. Filter 152 is a passband filter tuned to the casing thickness resonance frequency of the casing 12 under acoustic investigation. The passband for filter 152 preferably is narrow with sharp rising and falling slopes. The filter 152, however, should be sufficiently wide in its frequency band to overlap the frequency range of dips 142 for the expected tolerance variations in casing thickness. Generally, a filter 152 with a passband of about 10% to 15% of the center frequency would suffice, though a smaller passband of about 5% may provide a dip amplitude indication on line 156. A digital as well as analog filter 152 may be used.

Filter 154 preferably is tuned to a separate non-overlapping segment of the spectrum of the signal on line 63 to provide a reference signal on line 158 indicative of the amplitude of the spectrum of the signal on line 63. Other devices can be employed to derive such reference signal such as the peak detection technique described with reference to the embodiment in FIG. 1. The dip amplitude signal on line 156 is thereupon normalized by dividing this signal by the reference on line 158 with a divider network 160. A normalized dip value signal is then available on the output 162 of divider 160 to provide an indication of the quality of the cement bond for recording or plotting as the case may be.

FIG. 8

FIG. 8 illustrates another embodiment for determining the cement bond. The output from transducer 36 on line 63 from amplifier 62 (see FIG. 1) is applied to a high speed analog to digital (A/D) converter 172 which is actuated a specified time after an acoustic pulse. This produces a digitized reflection signal formed of sequential numerical samples representative of the amplitude of the reflection signal. The A/D converter may be deactived a certain time period following generation of an acoustic pulse.

A/D converter 172 is located downhole in tool 10 and is capable of operating at a very high speed and is provided with sufficient storage capacity to initially store and subsequently transmit the samples at a slower rate to a surface located signal processor 174. The latter could, if desired be also located in tool 10, but this would depend upon the scope of operations the signal processor 174 must perform.

The sampled digital reflection signal is stored in a memory 176 which may be a solid state memory or a magnetic memory. The memory 176 can be an integral part of processor 174 for immediate processing of the samples or be a peripheral device which is accessed at a later time after logging of the borehole 16.

Signal processor 174 may be programmed to select, at 178, those reflection samples, $A_c$, representative of the casing reflection 70 (see FIG. 4). The procedure can be similar to that illustrated in analog form in FIG. 1. Thus the reflection samples are scanned to detect the first sample which exceeds a predetermined threshold and this first sample becomes the arrival time of the casing reflection. A certain number of samples following this first sample are then selected as representative of the casing reflection 70 (see FIG. 4).

A certain number of reflection samples, $A_r$, following the casing reflection samples $A_c$ are selected at 180 as representative of the reverberation segment 72 in the reflection signal (see FIG. 4).

Integration of the reverberation samples is done by summing the absolute values of the samples at 182. This summing step could be carried out as the reverberation samples are selected at 180. However, for purposes of clarity, the summing operation is shown as a separate step. The integrated sum $E_R$ is stored.

Integration of the casing reflection samples $A_c$ is obtained at 184 by summing the absolute sample values and storing the result, $E_c$.

A normalized bond value, CB, representative of the quality of the cement bond may then be obtained at 186 by dividing the integral $E_R$ by the integral $E_C$ at 186. The bond value CB may be recorded in memory or plotted as desired at 188.

Figure 10:
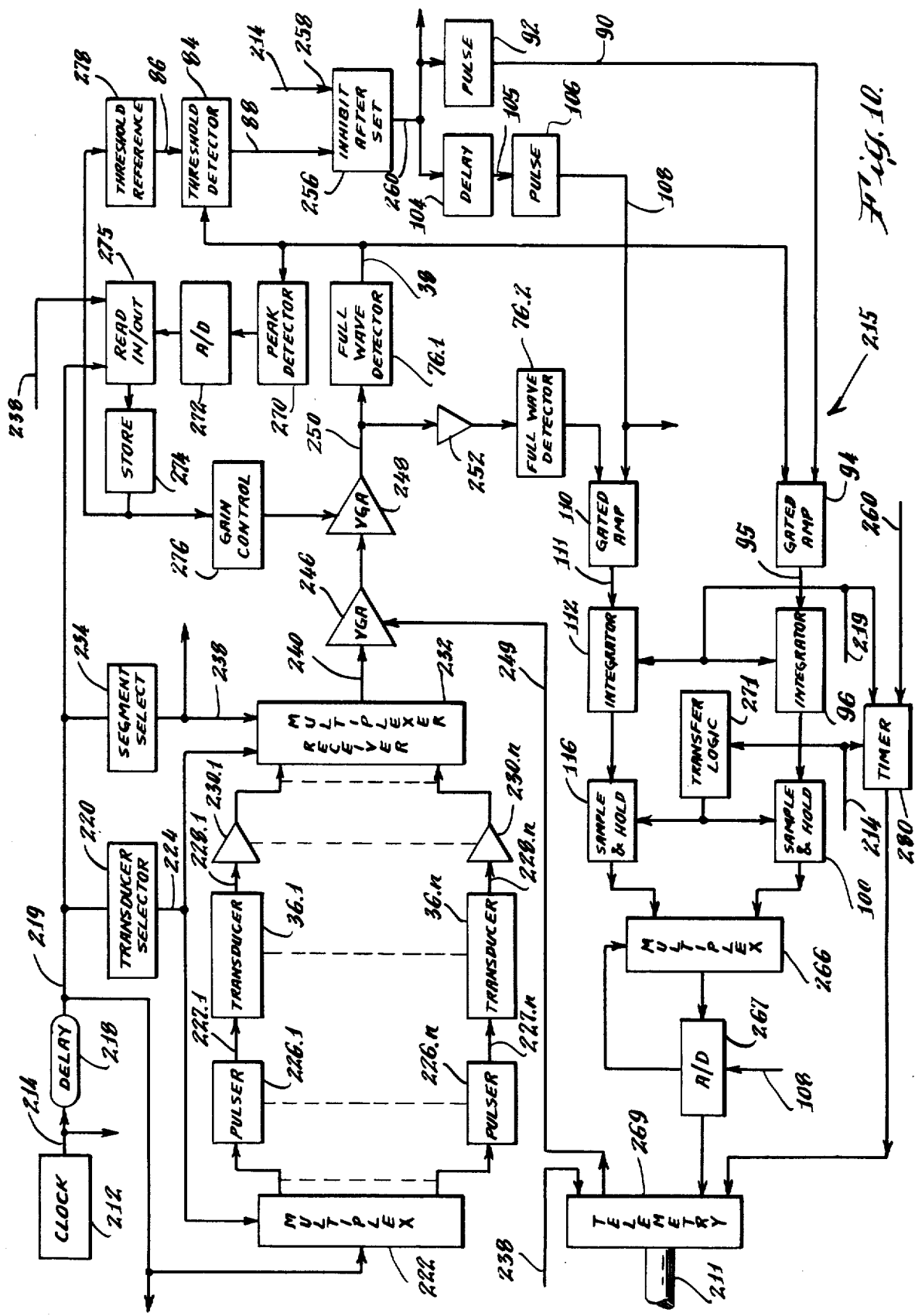
FIG. 10 is a block diagram of a signal processor for use with a cement bond evaluation tool of a type such as shown in FIG. 9.
Figure 11:
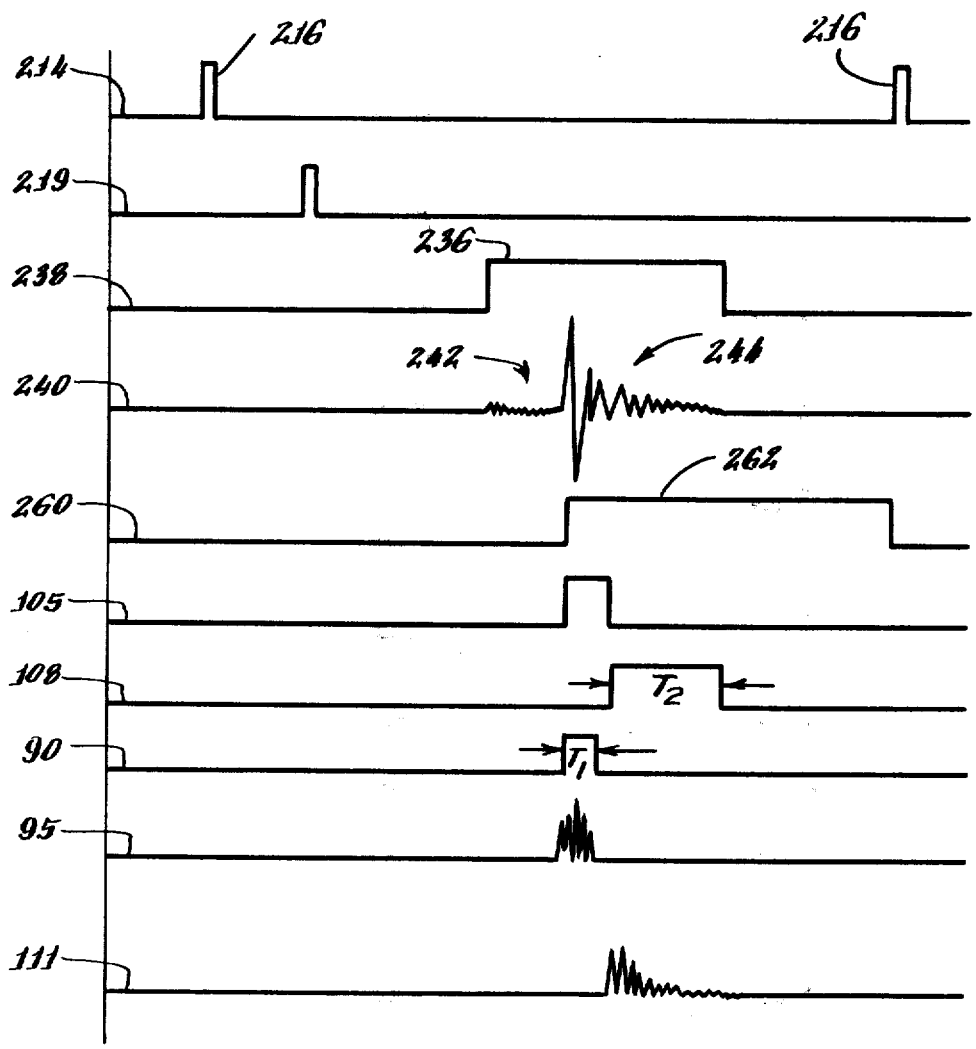
FIG. 11 is a timing diagram of signals generated in the signal processor shown in FIG. 10.

FIGS. 9, 10 and 11

FIG. 9 illustrates still another embodiment for investigating the quality of the cement bond. A tool 210 suspended from a cable 211 is provided with a plurality of transducers, such as 36, but arranged circumferentially around the tool 210 to provide sufficient circumferential cement bond evaluation resolution. The transducers 36 are axially spaced to accommodate the large number. A practical number of transducer 36 may be eight which are circumferentially spaced at 45° intervals. The axial spacing is selected commensurate with the size of the transducer 36.

FIGS. 10 and 11 relate to a signal processor 215 for operating a tool such as 210 shown in FIG. 9. The signal processor 215 is described useful for a tool 210 employing eight transducers 36; however, a greater number of tranducers can be accommodated. The signal processor 215 has an adjustable clock 212 on whose output 214 are pulses 216 (see FIG. 11) at a rate selected to determine the resolution of the cement bond investigation. The clock source may be derived from above ground devices or from a suitable oscillator located in the tool 210.

The clock pulses 216 are applied through a delay network 218 to a transducer selector 220 and a transmitter pulse multiplexer 222. The transducer selector 220 provides a discrete output enabling signal on line 224 to identify each different transducer 36 in succession. Hence, multiplexer 222 is enabled to sequentially fire pulsers 226 coupled to transducers 36.

The transducers 36 also act as receivers and produce signals on output lines 228 for amplification in pre-amplifiers 230 operatively associated with each transducer 36. The output of amplifiers 230 are connected to a receiver multiplexer 232 which is controlled by the transducer identifying signals on line 224 from transducer selector 220. In addition, a segment selection network 234 is activated with each transducer firing to generate enabling signals 236, see FIG. 11, on an output 238 to effectively enable multiplexer 232 to select the desired segment from the transducer outputs while rejecting or blanking out the initial transmitter segments. The output 240 from multiplexer 232 will have an appearance as illustrated at 244 in FIG. 11. A small noise signal 242 precedes the reflection signal 244 which has an appearance generally as illustrated in FIGS. 4A-4C.

Returning to FIG. 10, the reflections on output line 240 are amplified by two variable gain amplifiers (VGA) 246, 248. Amplifier 246 has its gain controlled by a signal on libne 249 and derived from either above ground equipment to adjust for mud attenuation effects or from a down hole automatic gain control. The second amplifier 248 has its gain atuomatically controlled in tool 210 to adjust the eccentering of tool 210 as will be further explained.

The output 250 from amplifier 248 is rectified in a network 76.1 and applied to a casing reflection sensing network formed of gated amplifier 94, integrator 96 and sample and hold network 100 as described with reference to FIG. 1.

The output on line 250 from amplifier 248 is further amplified in an amplifier 252 by a sufficient amount to compensate for the approximate difference in signal amplitude between the casing reflection and the acoustic returns indicative of subsequent reverberations. An acceptable compensation may be a gain factor of about 20 db for amplifier 252. The reflections of interest are then applied to a full wave rectifier 76.2 for subsequent integration with devices as described with reference to FIG. 1.

Control over the gating amplifiers 94, 110 is derived generally as described with reference to FIG. 1 with a threshold detector 84 responsive to the output on line 78 from full wave detector 76.1. A reference threshold value is derived on line 86 as a result of a similar previous cement bond investigation made with the particular transducer as shall be further explained.

The output 88 from threshold network 84 is applied to the set input of a latch network 256. Network 256 has a reset input 258 responsive to the clock pulses on line 214 (before the delay from network 218). When the threshold detector senses a signal on line 78 greater than the reference value on line 86, a pulse is applied to network 256 which thereafter is inhibited from responding to further inputs from the threshold detector until network 256 is reset by a pulse on line 214. The output on line 260 will have the appearance as shown with pulses 262 (FIG. 11) having an active state upon the occurrence of the large casing reflection.

The integration times, $T_1$ and $T_2$ (see also FIG. 11), for signals representative of the casing reflection and the reverberations are derived with pulse networks 92 and 106 respectively, whose outputs 90, 108 are applied to enable gating amplifiers 94, 110. The duration and occurrence of the integration periods $T_1$ and $T_2$ are respectively about 8 microseconds for the casing reflection and about 30 microseconds for the reverberations.

Subsequent integration of the casing reflection signal by integrator 96 and the reverberation segment by integrator 112 are terminated at the end of pulses $T_1$ and $T_2$ when the output from amplifiers 94, 110 go back to zero. The integrator outputs are sampled at the end of pulse $T_2$ and the samples made available for further processing with a suitable multiplexer 266 for transmitting the samples to above ground equipment. Transmission of information may employ an analog to digital converter 267 and suitable telemetry equipment 269 for transmission up cable 24. The integrators 96, 112 are reset by pulses on line 219 and the sample and hold network by pulses on line 214 from transfer logic 271 at the time of clock pulses 214.

As previously mentioned, the gain control for amplifier 248 is automated by sensing the peak value of the casing reflection on line 78 with a peak detector 270. The peak value is then converted to a digital value with A/d converter 272 and this value placed in a storage network 274 in a location associated with the transducer from which the reflection was obtained. The next time this transducer is energized, the transducer selector 220 provides an appropriate address signal to a read-in read-out logic network 275 to apply the previously stored peak value to a gain control network 276 and a threshold reference signal producing network 278.

For gain control the digital peak value is converted to an analog signal and an appropriate bias applied to control the gain of amplifier 248. In a similar manner, the threshold reference value on line 86 is maintained at the appropriate level for each transducer 36.

The techniques employed in evaluating the cement bond as described herein advantageously enable accurate measuring of the eccentricity of the tool as it moves along the casing. This technique as shown in FIG. 10 involves a timer 280 which is energized each time a transducer 36 is initially fired. The timer 280 is deactivated to store a measured time interval when a casing reflection is detected by the threshold detector 84 as evidenced by the signal on line 260. The measured time intervals for the various transducers should be the same and any difference may then be attributed to an off-center position of the tool. The output of timer network can be recorded or plotted and suitable processed to measure and locate the eccentricity of tool 210.

The vertical resolution of the tool 210 is a function of the repetition rate with which the transducers 36 are energized and produce detectable casing reflections and reverberations. A repetition rate as high as 100 per second can be accommodated to yield a resolution as small as about every one-tenth of an inch when the tool is moved at a logging rate of about 10 inches per second along the casing. A signal on line 213, see FIG. 9, representative of the depth of tool 210 is obtained to enable a signal processor 215 to adjust for the difference in levels of transducers 36.

Figure 12:
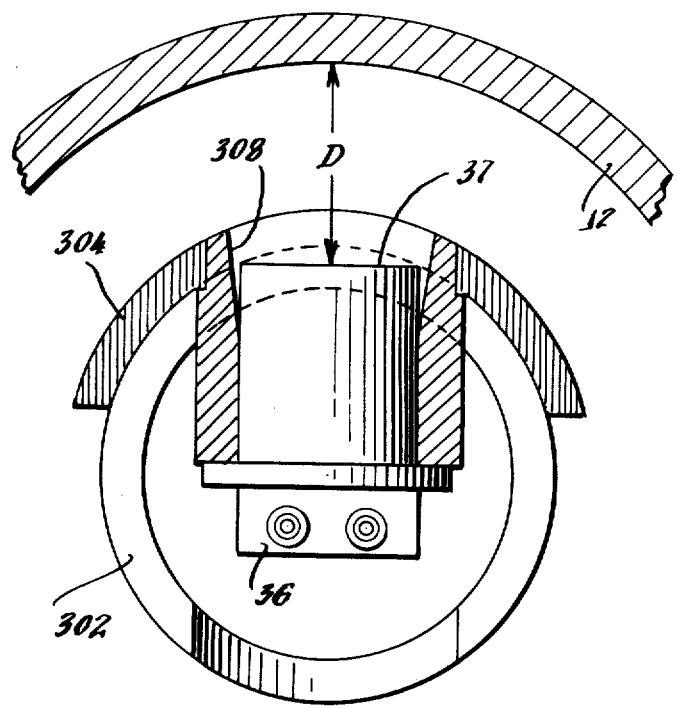
FIGS. 12 and 13 are top views in partial section of transducers for use in a tool such as shown in FIG. 9.
Figure 13:
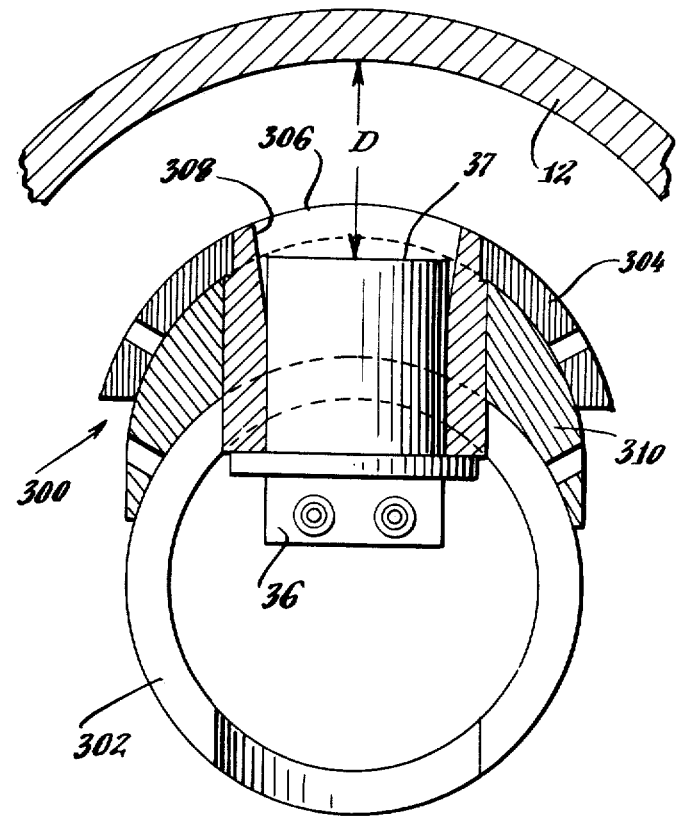
Figure 14:
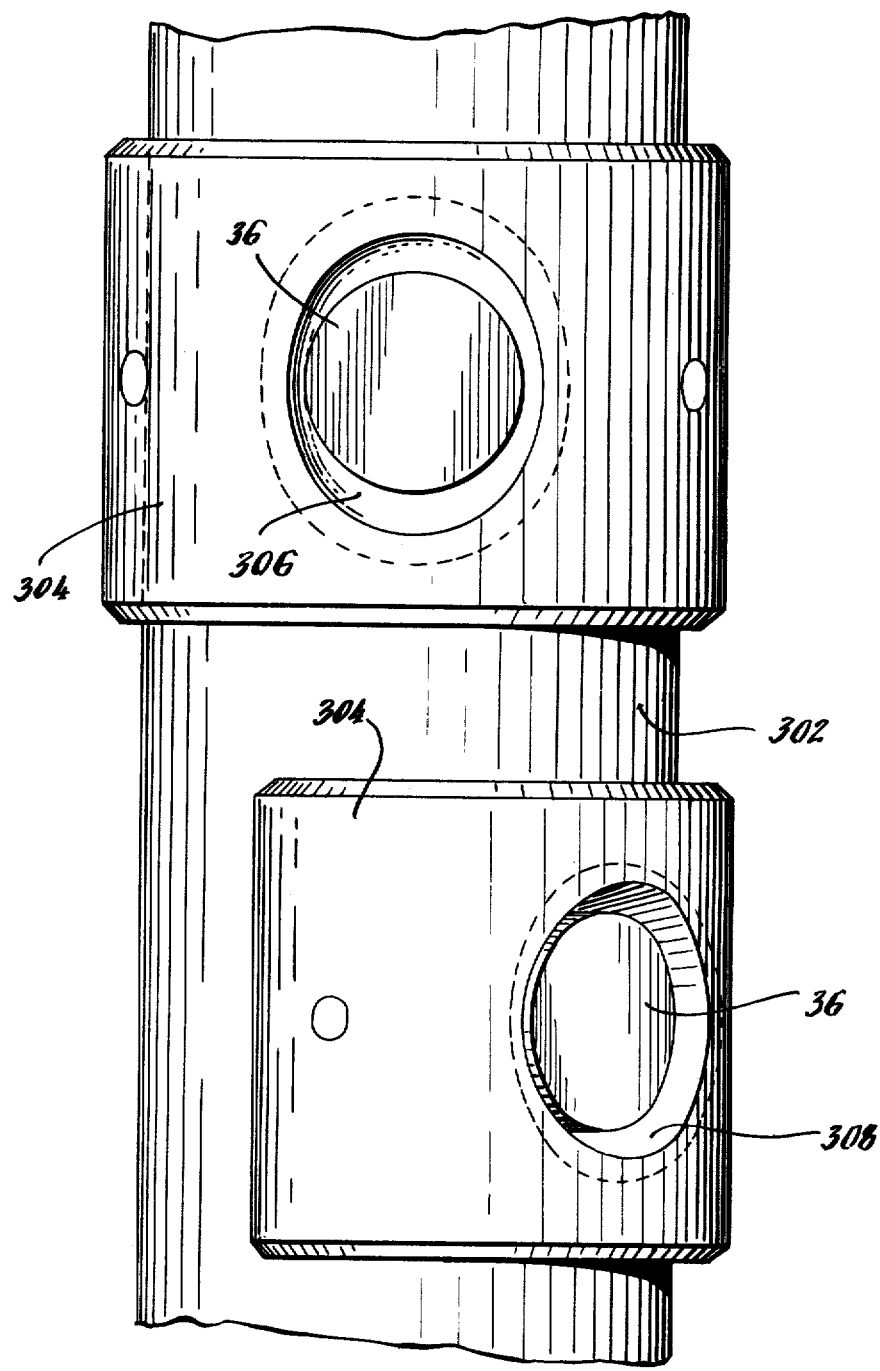
FIG. 14 is a partial side view in elevation of an acoustic investigation tool employing transducers as shown in FIGS. 12 and 13.

FIGS. 12, 13 and 14

FIGS. 12, 13 and 14 illustrate an acoustic energy source and detector 300 for multiple use on a tool such as shown and described with reference to FIG. 9. The detector/source 300 is radially mounted to a cylindrical housing 302 with a mounting bracket 304 having a central aperture 306 to receive a cylindrical or disk transducer 36. The mounting bracket 304 extends past the emitting surface 37 of transducer with a lightly outwardly expanding aperture wall 308.

Bracket 304 may be directly mounted to housing 302 such as shown in FIG. 12 or with an intermediate spacer 310 as shown in FIG. 13. In the mounting of FIG. 12, the transducer to casing spacing D can accommodate smaller casings, say from about 5½ inch diameter. The arrangement of FIG. 13 can accommodate larger casings.

The radial orientation of transducers 36 preferably involves no window or intermediate materials. Furthermore, the spacing D between the transducer face 37 and casing 12 is kept as small as possible.

Since too small a spacing D enables secondary transmissions to interfere with the reflections of interest, the spacing D cannot be too small. On the other hand, if the spacing D is too large, mud attenuation effects can be too large as well. Hence, a compromise spacing D may be selected based upon expected attenuations.

The attenuations may vary depending upon the type of mud used. For example, a heavy or dense mud may cause an undesirably high attenutation. Hence, in the selection of an acceptable spacing D, it may be necessary to also specify an upper and mud density limit. With such upper limit, the maximum attenuation may be about 4 to 5 db per inch in contrast with a heavy mud attenuation of about 8 to 10 db per inch.

With these general constraints, an acceptable spacing D may be of the order of about one to about two inches for most casings.

The described arrangement for tool 20 with a rotatable reflector 38 may be varied in a number of ways. For example, in some instances it may be desirable to mount the reflector 38 in a pad near the wall of casing 12 to reduce the attenuation effect of a dense mud fluid. Care should be exercised to assure that the reflector 38 remains sufficiently spaced from the wall of the casing 12.

FIGS. 15 and 16 and 6

Casing thickness is measured by analyzing the frequency spectrum of the reverberation segment 72 (see FIG. 4A) representative of acoustic returns attributable to reverberations between the casing walls 13-13'. When an acoustic pulse such as 50 is directed at the casing 12, a substantial amount of acoustic energy at the resonance frequency is trapped inside the casing walls.

The reverberation segment 72 has predominant components in a frequency portion 320 (see FIGS. 6A-6C) generally in frequency alignment with dips 142. The dips 142 increase in depth as the quality of the cement bond decreases, but the amount of energy trapped in between the casing walls increases with poorer bonding between the cement and the casing. Hence, the actual amplitude of the acoustic returns in the frequency portion 320 will vary. Generally, the actual amplitude of the acoustic reverberations within the frequency portion 320 reduce as the acoustic coupling between casing 12 and cement 14 becomes more efficient; i.e. as the cement bond becomes better.

This is illustrated in the spectrum plot of FIG. 16 with curves 322 and 324 which respectively illustrates the frequency spectrum of a frequency portion 320 for a bad cement bond and a good cement bond.

When thin spots develop in casing 12 such as at 33.1 and 33.2 in FIG. 15, they are likely to affect the cement bond evaluation. The effect of such thin spots upon the cement bond is not easy to predict and appears likely to be a function of such factors as size and cement conditions. For example, there is no cement bonding behind the thin spot 33.1, but since the casing is substantially thinner here, less acoustic energy remains trapped inside the casing walls 13—13' than in case of a normal thickness so that the thin spot 33.1 may appear as a good bond. On the other hand, if an isolated external thin spot such as 33.2 occurs at a well bonded area the casing 12 may appear as poorly bonded. Hence, it is advantageous to be able to correlate a casing thickness measurement with an evaluation of the cement bond to remove ambiguities.

The measurement of casing thickness is done in the apparatus 326 of FIG. 15 by forming a frequency spectrum of the reverberation segment as derived on line 63 of FIG. 1. The frequency spectrum is characterized by one or more peaks of which the largest occurs at a fundamental frequency whose wavelength is twice the thickness of the casing. Other peaks occur a frequencies which bear a whole multiple relationship to the fundamental frequency.

FIG. 16 illustrates several frequency spectra 322, 324 of several reverberation segments 72 selected from different signals. It should be understood that in the presentation of the various spectra in FIG. 16, there is no intent to set forth an amplitude relationship between the spectrum 52 of the acoustic pulse 50 (see FIGS. 2 and 3) and the other spectra 322, 324; rather, it is only intended to show a frequency relationship in that the spectra 322, 324 occur within the frequency bandwidth of the incident acoustic pulse. In practice, the absolute amplitudes of the acoustic spectra would be quite small in comparison with that of the transmitted pulse.

Of particular interest is the relative frequency shift between the spectra peaks 328, 330. The frequency difference between peaks 328, 330 can be attributed to a change in the thickness, L, of casing 12. Hence, by determining the frequency of the peaks predominantly attributable to acoustic returns from the reverberations between the casing walls, an indication of the casing thickness can be obtained.

The casing thickness, L, can be derived from the following relationship $L = N(C/2f_p)$, where $f_p$ is the frequency of the peak in the spectrum, C the compressional velocity in the casing 12 and N is a whole integer depending upon whether the measured peak is for the fundamental frequency ($N=1$) or a higher harmonic.

Since the frequency spectrum 52 of the acoustic pulse 50 has a bandwidth of from about 300 to 600 KHz for use with casings 12 over a wide range of thicknesses, from about 0.2" to about 0.75", the second harmonic ($N=2$) is likely to produce the largest peak in the reverberation spectra for the thicker casings while $N=1$ for the thinner casings. The value for N, therefore, can be determined prior to an acoustic investigation from a knowledge of the type of casing installed in the borehole.

For example, an installed casing is known to have a nominal thickness of 0.362 inches, so that its fundamental thickness resonance occurs at about 331 KHz for a value of C of 20,000 ft/sec. As actually measured, the spectrum 322 may present a peak 328 at a frequency of $f_{p2}$ of about 348 KHz corresponding to an actual casing thickness of 0.345 inches in one radial segment of the casing. Spectrum 324 presents a peak 330 at a frequency $f_{p1}$ of about 303 KHz corresponding to an actual casing thickness of 0.395 inches. These measurements illustrate the resolution of the technique by detecting a casing thickness variation of about ±7% due to manufacture from the nominal value of 0.362 inches.

In apparatus 326 of FIG. 15 the casing thickness is measured by selecting the reverberation segment 72 on a line 332 with a selection network 334 coupled to the reflection signal on line 63. The selection network 334 employs a casing reflection detector 336 to provide on output 338 a pulse whose leading edge is representative of the start of the casing reflection 70 (see FIG. 4). Detector 336 may be formed of a threshold detector 84 for rapid response or as shown in FIG. 1 of a full wave rectifier 76, filter 80 and threshold detector 84.

The pulse on line 338 is delayed by a delay 340 for a time period commensurate with the duration of the strong initial casing reflection 70 to then actuate a pulse network 342. The latter produces a reverberation segment selection pulse on line 344 to enable an analog gate 346 for a duration corresponding to the time needed to select the portion of the reflection signal predominantly representative of reverberations inside the casing walls.

A spectrum analyzer 384 is responsive to the reverberation segment on line 332 to provide on line 350 a signal representative of the amplitude, A, of the frequency components in the reverberation segment 72 while output line 352 carries a corresponding frequency signal, f, representative of the frequency of the amplitude components on line 350.

The amplitude and frequency signals on lines 350, 352 are individually applied to analog to digital converters 354, 356 which produce and store in a memory 358 of a signal processor 360, the digital signals representative of the amplitude A$_i$, and frequency, f$_i$, of the frequency spectrum of the reverberation segment 72.

The operation of spectrum analyzer 348 and A/D converters 354, 356 is initiated by the reverberation segment selection pulse generated on line 344 from pulse network 342. During the latter pulse, a local oscillator, internal to spectrum analyzer 348, is repeatedly swept through a frequency range to produce the amplitude spectrum on line 350. Each time the local oscillator is swept through its frequency range, spectrum analyzer 348 generates a spectrum field of amplitude, A$_i$, and frequency, f$_i$, signals. Hence, during the selection of a single reverberation segment 72 a plurality of spectrum fields are generated and stored in memory 358.

For a non-recurring reverberation segment 72, a discrete multiple of sweeps of the local oscillator in the spectrum analyzer 348 can be sufficient to derive an indication of the frequency spectrum. The A/D converters 354, 356 are of such type that an adequate number of conversions can be made during each sweep of the local oscillator.

Once the spectrum fields formed of frequency, f$_i$, and amplitude, A$_i$, signals are stored in memory 358, signal processor 360 is actuated to search for a peak amplitude value, A$_p$, at 362. This is done by searching all of the stored amplitude values, A$_i$, and comparing each with the next amplitude value and retaining the larger amplitude value for the next comparison. By preserving the frequency value, f$_i$, associated with each each retained amplitude value, the frequency, f$_p$, of the peak A$_p$ can be found and both are appropriately stored at 364.

In certain instances several peaks may occur in the stored spectrum samples. Although the largest peak is used to derive a thickness determination, one may also employ both peaks for this and select the casing thickness measurement which is closest to the nominal value as the proper measurement.

The detected peak values, both amplitude, A$_p$, and frequency, f$_p$, may then be recorded such as on plotter 122. The frequency, f$_p$, may be recorded directly as an indication proportional to casing thickness, L, or the latter may be computed on the basis of the previously described relationship and then recorded. Other information may be simultaneously recorded on plotter 122 such as well depth on line 24, the cement bond signal on line 120, azimuth of a rotational scanning reflector on line 37 to identify the depth and circumferential location of the radial casing segment whose thickness was measured.

FIG. 17

Figure 17:
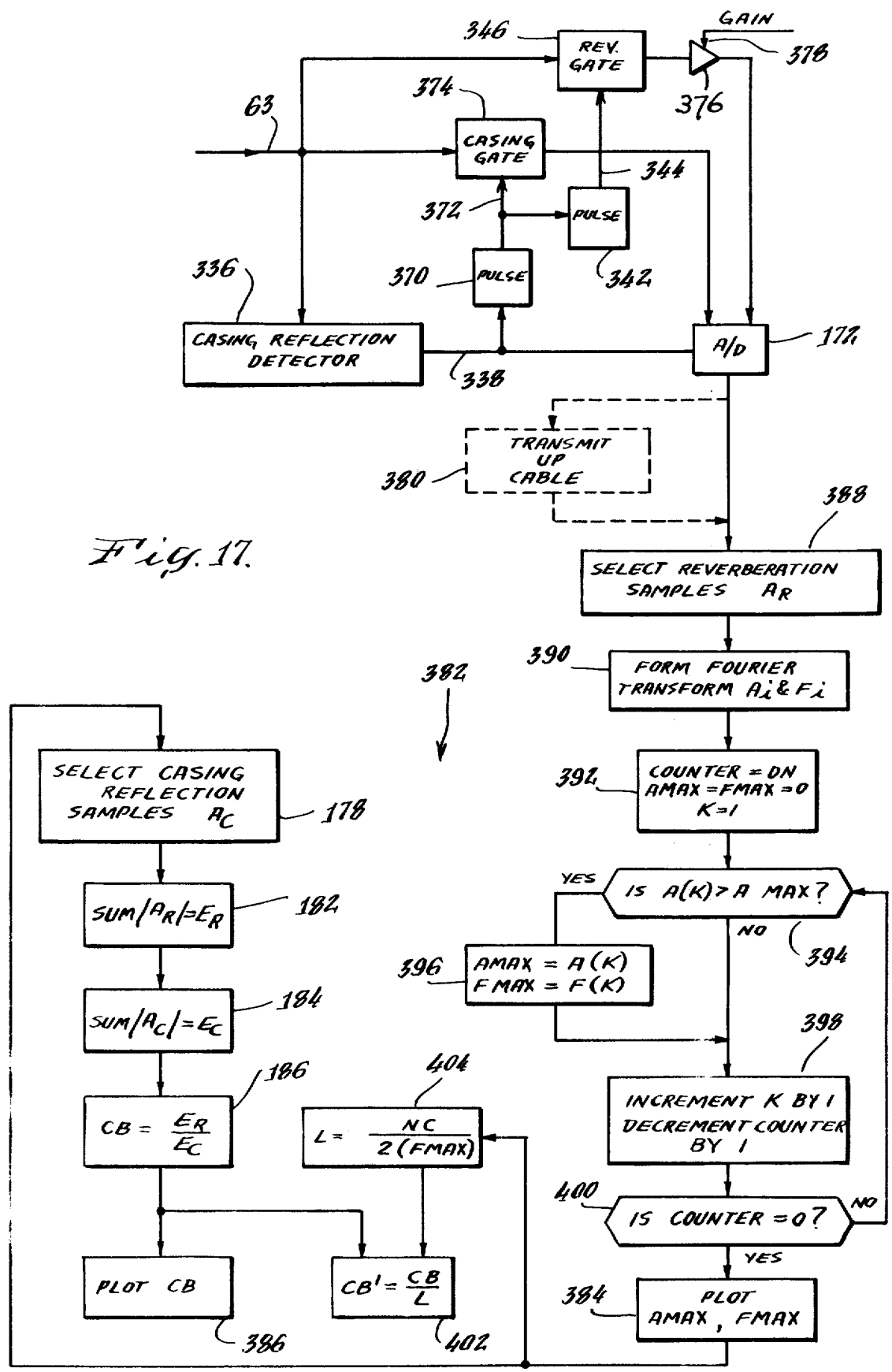
FIG. 17 is a block diagram of a signal processing apparatus for determining the quality of the cement bond and casing thickness in accordance with the invention.

In an alternate embodiment for determining casing thickness as shown in FIG. 17, the entire reflection signal on line 63 as digitized as described with respect to FIG. 8 for the evaluation of the cement bond. The digitizing process is commenced upon the detection of the arrival of the casing reflection by detector 336 which is described with reference to FIG. 15.

The output pulse on line 338 from detector 336 is a pulse of sufficient duration to enable digitizing of an entire reflection signal such as 64 (see FIG. 4A). This pulse activates a network 370 which generates a pulse on line 372 with a duration generally about equal to that of the casing reflection segment 70 shown in FIGS. 4. The pulse on line 372 in turn closes an analog casing logic 374 for this time period to pass the casing reflection segment 70 onto A/D converter 172. The latter digitizes the casing reflection segment 70 and stores the samples in a suitable memory (not shown).

When the casing reflection segment has passed, the pulse on line 372 goes inactive which, in turn, activates a network 342 to provide an enabling pulse on line 344 to permit analog reverberation gate 346 to pass a reverberation segment 72 through an amplifier 376, having a gain controlling input 374, to A/D converter 172.

The amplifier 376 permits amplification of the normally weak reverberation segment 72 for more precise signal processing. The digitized reflection signal may be processed downhole or transmitted up the cable with a suitable telemetry device 380.

A signal processor 382 is provided to operate on the digitized reflection signal from A/D converter 172. The processor 382 provides a casing thickness determination at 384 and a cement bond evaluation signal, CB, at 386.

The casing thickness is determined by selecting the reverberation samples A$_R$ at step 388 and generate a spectrum thereof at 390 with a fourier transformation. The spectrum is formed of amplitude values A$_i$ and associated frequency values F$_i$.

The spectrum is then scanned to select the maximum peak value. This may be done by setting, at 392, a counter equal to the number, DN, of reverberation samples, a constant K=1 and the values of AMAX and FMAX equal to zero.

A test is made at 394 whether the amplitude value A for the sample K is greater than AMAX. If so, then the values for AMAX and FMAX are made equal to A(K) and F(K) at 392. The next samples may then be examined by incrementing K and decrementing the counter by one at 398 and testing for whether the counter is equal to zero at 400.

If not all of the samples have been scanned, the counter is not equal to zero and the search for a maximum spectrum value is repeated at 394. Once all of the samples have been scanned, the maximum values, AMAX and FMAX can be plotted at 384 or the casing thickness, L, derived from the formula $$L = N \frac{C}{2(FMAX)}.$$

A cement bond evaluation can be conveniently made by signal processor 382 utilizing the steps as described with reference to FIG. 8.

The cement bond signal CB varies as a function of casing thickness. This variation can be substantially removed from the cement bond signal at 402. This involves dividing the cement bond signal CB by a casing thicknss signal L as determined at 404 from the frequency measurement FMAX using the casing thickness relationship as previously explained.

This normalization of the cement bond signal removes variations due to directly proportional casing thickness changes, leaving lesser second order casing thickness effects. The cement bond for a particular radial segment can thus be advantageously evaluated in a manner which is substantially insensitive to the casing thickness at the same radial segment. Cement bond normalization relative to casing thickness may also be carried out directly with a cement bond signal such as available at 182 in FIG. 17 or on line 117 in FIG. 1 before normalization by the casing reflection signal. The latter signal may then be employed to further normalize the cement bond evaluation as described.

FIG. 18

FIG. 18 shows an alternate embodiment for deriving the frequency of a peak in the spectrum of a reverberation segment 72. The outputs 350, 352 from spectrum analyzer 348 (see FIG. 15) are recorded on continuous tracks 410.1, 410.2 of a storage medium 412 such as a magnetic disc or drum. After recording the output from analyzer 348 for a reverberation segment 72, the information is played back for analysis for an associated signal processing network 414 to detect, store and record the amplitude and frequency peak values, $A_p$ and $f_p$.

The spectrum analyzer outputs 350 and 352 are shown coupled through logic amplifiers 416, 418 to record/playback heads 420, 422 operatively disposed with respect to magnetic storage disc 412. The amplifiers 416, 418 are enabled by the segment select pulse on line 344 (see FIG. 15). The amplitude, A, and frequency, f, signals are recorded on separate continuous tracks 410.1, 410.2 which have sufficient recording length to record an entire reverberation segment 72.

After recording of the reverberation segment, logic playback amplifiers 424, 426 are enabled, by virtue of the removal of the disabling effect of the pulse on line 344 through inverter 428. This then permits playback of the previously recorded amplitude, A, and frequency, f, signals.

A peak detector 430 is provided to scan for the peak value in the amplitude signals played back through amplifier 424. The detected peak value is then applied to a comparator 432 together with another playback of the previously recorded amplitude signals on track 410.1 to enable the determination of the frequency, $f_p$, at the time the peak occurs.

When comparator 432 recognizes equality between its inputs, a pulse is produed on output line 434 to activate a sample and hold network 436 coupled to sample the played back frequency signal, f, from amplifier 426. The frequency, $f_p$, of the amplitude peak value is then stored and made available on output line 438 for recording and use as an indication of the thickness of the casing 22 as previously described.

The recording, peak scanning and peak frequency selection are carried out in sequence under direction of control signals on line 440 from a control logic network 442. This network is initiated by the pulse on line 344 and subsequently by the playback of a recording of like pulses derived from a control track 410.3 on magnetic storage medium 412.

Figure 19:
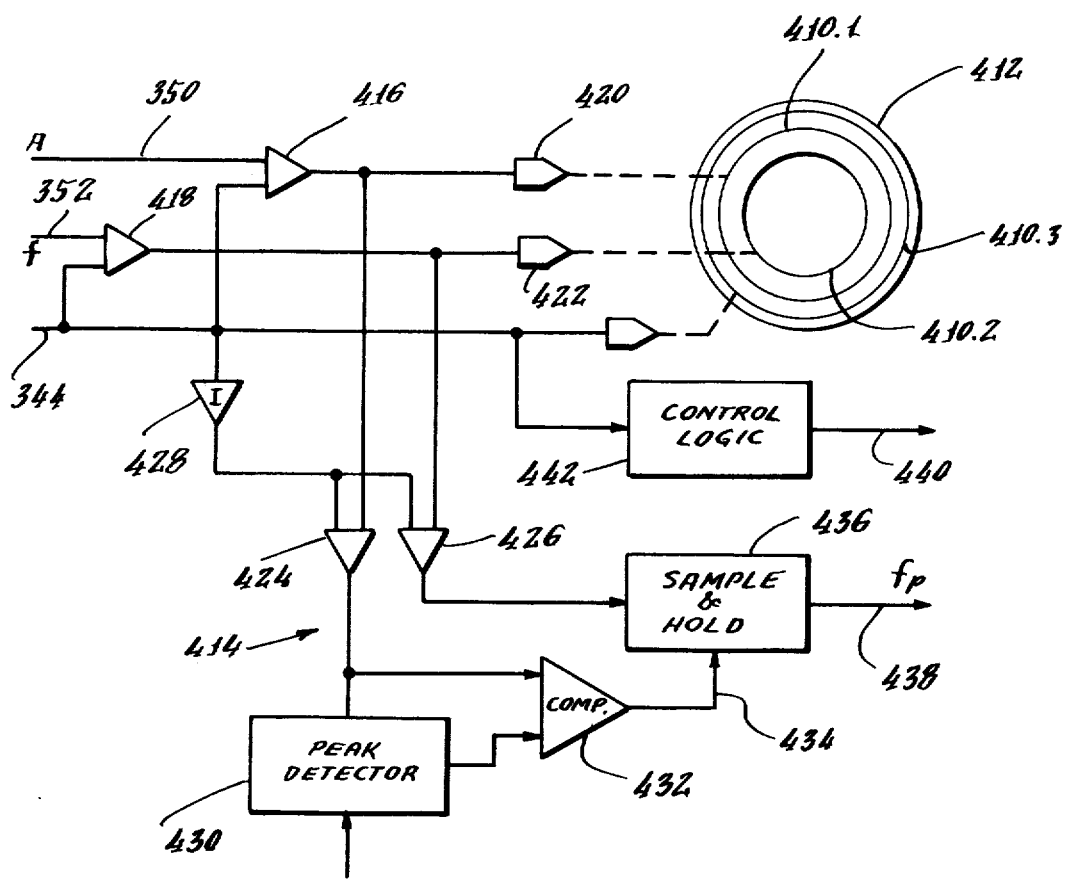
FIG. 19 is a sectional view of an acoustic borehole investigating tool employing a rotating reflector for scanning of the borehole.

FIG. 19 illustrates another form 460 for an acoustic cement bond and casing investigating tool, wherein as in FIG. 1, a rotating reflector 38 is employed. The tool 460 is provided with a stationary transducer 36 and a longitudinal cylinder 462 centrally and rotatably mounted relative to tool 460 about a rotational axis 464 which in this embodiment is preferably coincident with the central tool axis.

The tool 460 has an annular acoustically transparent window 466 mounted between an upper tool section 468 and a lower tool section 470. The cylinder 462 internally bridges the window 466 and rotationally engages the upper and lower sections 468, 470 through bearings 472. The cylinder 462 has a tubular section 474 into which transducer 36 projects through an open end at 476. The tubular section 474 terminates at reflector 38 from where the cylinder 462 preferably is solid down to its end 476. Cylinder 462 is provided with a pair of annular radially extending flanges 478.1 and 478.2. Bearings 472 are clamped against flanges 478 with annular bushings 480 affixed to tool sections 468, 470 with screws such as 482. Bearings 472 fit in axially open annular grooves 484, 486 in flanges 478 and bushings 480 respectively. Bearings 464 provide both thrust and radial low friction support. Additional bearings and flanges can be employed if needed.

Cylinder 462 is of rugged strong construction to reinforce the lower tool section 470 to which a load producing device, such as an externally mounted centralizer (not shown), can be applied. The cylinder 462, thus serves as a strong reinforced bridge over acoustic window 466. The ability to employ a centralizer below the rotating reflector 38 enables a precise placement of the rotational axis 464 relative to the casing 12 and thus preserve an accurate spacing of reflector 38 from casing 12.

The acoustic reflector 38 has a reflection angle $a$ of a magnitude necessary to enable acoustic communication through a side-located opening 490 in tubular section 474. In front of opening 490 and contiguous with the outer wall of upper tool section 468 is the acoustic window 466 formed of a material having a predetermined acoustic impedance and provided with a shape selected to minimize unesirable acoustic reflection.

The acoustic window 466 is formed of a material whose acoustic impedance closely matches the acoustic impedance of a fluid, such as described with reference to FIG. 1, and which is placed in the space between source 36, reflector 38 and window 466. The acoustic temperature and pressure coefficients, i.e. the change in acoustic impedance as a function of temperature and pressure for both the fluid and the window 466 are selected as close as practically possible. The acoustic window 466 can be made of a material as described with reference to window 40 in FIG. 1 or of polysulfone, a material sold by the Union Carbide Corporation under the trade name RADEL and having an acoustic velocity of about 2200 meters/second. Hence, as an acoustic pulse is generated from source 36 towards reflector 38, the acoustic energy passes through the fluid/window interface 492 with a minimum of reflection.

In order to further reduce the effect of acoustic reflections from a window interposed between the source 36 and casing 12, the window is conically shaped with an inclination angle $\theta$ relative to reflector 38 as described with reference to FIG. 1 to permit use of a large reflector 38 and also to deflect secondary transmissions away from the casing 12.

Transducer 36 in FIG. 19 is mounted to a bracket 494 attached to the wall of tool section 468. An electrical cable 496 connects transducer 36 to electronic circuitry (not shown).

A rotational drive for cylinder 462 is provided by an electrical motor 498 mounted inside tool 460 and having an output shaft 500. A gear coupling 502 interconnects the motor shaft 500 to the cylinder 462.

The gear coupling 502 may take a variety of different forms and is, for illustrative purposes, shown composed of a pair of pinions 504, 506, with the latter mounted to a shaft 508 journaled in a bushing 510 on bracket 494. A bevel drive, formed of 45° bevel gears, 512, 514, is used to interconnect the shaft 508 with cylinder 462.

With a tool 460 as shown in FIG. 19, the structural integrity of the tool is extended to below the annular window 466. This provides additional strength below the window and permits its centralization relative to casing 12 with a centralizer. Window 466 can be made sufficiently strong to withstand such twisting forces as may be coupled through from the rotating cylinder 462.

Having thus explained techniques for investigating a casing cemented in a borehole to evaluate the cement bond and casing thickness, the advantages of the invention can be appreciated. Variations from the described embodiments presented herein are for illustration, with the scope of the invention to be determined by the following claims.

I claim:

1. An apparatus for determining characteristics of a casing cemented in a borehole penetrating an earth formation from a reflection signal derived from an acoustic investigation of the casing with an acoustic pulse directed at a radial segment of the casing and formed of acoustic waves at frequencies selected to stimulate a thickness resonance inside the casing walls comprising means for selecting from the reflection signal a reverberation segment substantially representative of acoustic reverberations between the casing walls at said radial segment;

means for determining the energy in the selected reverberation segment and producing a bond signal indicative thereof to characterize the quality of the cement bond behind said radial segment of the casing; and means for determining from said reverberation segment the frequency of components contributing to a peak value in the frequency domain of said reverberation segment and generate a casing thickness signal representative thereof as the casing thickness at said radial segment for the evaluation of the cemented casing and the resolution of potential ambiguities in the cement bond evaluation at said radial segment.

2. The apparatus as set forth in claim 1 wherein said means for producing a bond signal further includes means for determining the energy in a casing segment of the reflection signal representative of an acoustic reflection off an inner wall of the casing and provide a casing signal indicative thereof; and means for normalizing said bond signal with said casing signal to correct for borehole conditions.

3. The apparatus as set forth in claim 2 wherein said casing thickness signal generating means further includes means for producing a spectrum signal representative of the frequency spectrum of the reverberation segment; and means for scanning said spectrum signal for said peak value to derive the frequency of said components associated with said peak value.

4. A method for determining characteristics of a casing cemented in a borehole penetrating an earth formation from a reflection signal derived from an acoustic investigation of the casing with an acoustic pulse directed from inside the casing at a radial segment thereof and formed of acoustic waves at frequencies selected to stimulate a thickness resonance inside the casing walls comprising the steps of deriving from the reflection signal a reverberation segment substantially representative of acoustic reverberations between the casing walls at said radial segment;

measiuring the energy in the selected reverberation segment and provide a bond signal indicative thereof to characterize the quality of the cement bond behind said radial segment of the casing; and measuring the frequency of components contributing to a peak value in the frequency domain of the reverberation segment and provide a thickness signal indicative thereof as the casing thickness at said radial segment for the evaluation of the cemented casing and the resolution of potential ambiguities in the cement bond evaluation at said radial segment.

5. The method for determining casing characteristics as set forth in claim 4 and further including the step of recording said bond and said thickness signals as a function of borehole depth to provide a composite log for the correlation of the cement bond quality with casing thickness.

6. The method for determining casing characteristics as set forth in claim 5 wherein said reflection signal is in a digitized form composed of samples and wherein said energy measuring step further comprises summing absolute values of the samples representative of the reverberation segment as said bond signal; and wherein said frequency measuring step further comprises forming a fourier transformation of samples representative of the reverberation segment and composed of amplitude samples with associated frequency values;

scanning said amplitude samples for a peak thereof; and selecting an associated frequency value of the peak sample as a measurement of the thickness of the casing.

7. The method for determining casing characteristics as set forth in claim 6 wherein said energy measuring step further comprises summing absolute values of samples representative of the casing reflection produced by said acoustic pulse as an integral of said casing reflection; and forming a quotient between the respectively summed reverberation segment samples and the casing reflection samples to produce a normalized bond signal.

8. An apparatus for determining the quality of the bond between cement and a casing cemented in a borehole penetrating an earth formation from a reflection signal obtained from an acoustic investigation of the casing with an acoustic pulse directed at a radial segment of the casing and formed of acoustic waves at frequencies selected to stimulate a thickness resonance inside the casing walls comprising means for selecting from the reflection signal to the exclusion of a strong casing reflection signal, a reverberation segment substantially representative of acoustic reverberations between the casing walls at said radial segment; and means for determining the energy in the selected reverberation segment and producing a bond signal indicative thereof to characterize the quality of the cement bond behind said radial segment of the casing.

9. A method for determining the quality of the bond between cement and a casing cement in a borehole penetrating an earth formation from a reflection signal obtained from an acoustic investigation of the casing with an acoustic pulse directed at a radial segment of the casing and formed of acoustic waves at frequencies selected to stimulate a thickness resonance inside the casing walls comprising the step of measuring to the exclusion of a strong casing reflecting signal the energy in a reverberation segment of the reflection signal, wherein the reverberation segment is substantially representative of acoustic reverberations between the casing walls at said radial segment, and provide a bond signal indicative thereof to characterize the quality of the cement bond behind said radial segment of the casing.

10. The method for determining the quality of the cement bond as set forth in claim 9 wherein said reflection signal is in a digital form composed of samples and further including the step of summing absolute values of samples representative of the energy of the casing reflection; and dividing said bond signal by said sum for normalization thereof.

11. An apparatus for determining the quality of the bond between cement and a casing cemented in a borehoele penetrating an earth formation from a reflection signal obtained from an acoustic investigation of the casing with an acoustic pulse directed at a radial segment of the casing and formed of acoustic waves at frequencies selected to stimulate a thickness resonance inside the casing walls comprising means responsive to said reflection signal for detecting an initial casing reflection from the casing and produce a signal indicative thereof;

means actuated by the detected initial casing reflection signal for selecting from the reflection signal a reverberation segment substantially representative of acoustic reverberations between the casing walls; and means for producing a bond signal indicative of the energy in the selected reverberation segment to characterize the quality of the cement bond behind said radial segment of the casing.

12. The apparatus for determining the quality of the cement bond as set forth in claim 11 wherein said reflection signal is in the form of digital samples and wherein said means for producing said bond signal includes means for producing a sum of the absolute values of reflection signal samples representative of said reverberation segment as said bond signal.

13. The apparatus for determining the quality of the cement bond as set forth in claim 12 wherein said bond signal producing means further includes means for producing a sum of the absolute values of reflection samples representative of the initial casing reflection as a measure of the magnitude thereof; and means for producing a quotient between said sums to normalize the bond signal.

14. The apparatus for determining the quality of the cement bond as set forth in claim 13 wherein said means for producing said casing reflection signal includes a threshold detector effectively responsive to the reflecting signal to determine when said reflection signal exceeds a level representative of the presence of said initial casing reflection.

15. The apparatus for determining the quality of the cement bond as set forth in claim 14 wherein said threshold detector is formed of means for scanning samples of the reflection signal to determine the location of said initial casing reflection.

16. An apparatus for determining the thickness of a casing cemented in a borehole penetrating an earth formation from a reflection signal derived from an acoustic investigation of the casing with an acoustic pulse directed at a radial segment of the casing and formed of acoustic waves at frequencies selected to stimulate a thickness resonance inside the casing walls comprising means for selecting from the reflection signal a reverberation segment substantially representative of acoustic reverberations between the casing walls;

means for generating a spectrum signal representative of the frequency spectrum of said reverberation segment; and means for determining the frequency of components in said spectrum signal contributing to a peak value thereof and producing a thickness signal representative thereof as the casing thickness.

17. The apparatus for determining the casing thickness as set forth in claim 16 wherein the reflection signal is formed of digital samples and said spectrum generating means includes means for generating a fourier transform of samples representative of the reverberation segment as said spectrum signal.

18. A method for determining the thickness of a casing cemented in a borehole penetrating an earth formation from a reflection signal derived from an acoustic investigation of the casing with an acoustic pulse directed at a radial segment of the casing and formed of acoustic waves at frequencies selected to stimulate a thickness resonance inside the casing walls comprising the steps of generating a spectrum signal representative of the frequency spectrum of a reverberation segment of the reflection signal wherein said reverberation segment is substantially representative of acoustic reverberations between the casing walls at said radial segment; and measuring the frequency of components in said spectrum signal contributing to a peak value thereof and providing a thickness signal representative of said measured frequency as indicative of the casing thickness at said radial segment.

19. The method for determining casing thickness as set forth in claim 18 wherein the reflection signal is formed of digital samples wherein said generating step produces a spectrum signal formed of samples indicative of amplitudes and associated frequency values and wherein said measuring step further includes scanning said amplitude samples for said peak value and selecting the associated frequency of sample contributing to said peak as representative of the casing thickness.

20. An acoustic pulse echo apparatus for investigating a casing cemented in a borehole penetrating an earth formation comprising means for generating an acoustic pulse from inside the casing in a generally radial direction towards a selected radial segment of the casing wherein said acoustic pulse has a frequency spectrum selected to enhance entrapment of acoustic energy between the inner and outer casing walls at the radial segment for stimulation of reverberations therein and generating a reflection signal representative of acoustic returns from different layers of material in the path of the acoustic pulse with acoustic leakage from reverberations trapped inside said casing walls;

means for selecting a reverberation segment of the reflection signal wherein said selected segment is substantially representative of said reverberation leakage in the acoustic returns;

means for determining the energy in the selected reverberation segment and producing a bond signal indicative thereof to characterize the quality of the cement bond behind said radial segment of the casing; and means for determining from said reverberation segment the frequency of components contributing to a peak value in the frequency domain of said reverberation segment and generate a casing thickness signal representative thereof as the casing thickness at said radial segment for the evaluation of the cemented casing and the resolution of potential ambiguities in the cement bond evaluation at said radial segment.

21. The acoustic pulse echo apparatus for investigating a casing as set forth in claim 20 wherein the selecting means further includes means for detecting a casing segment in the reflection signal representative of an initial casing reflection produced by the acoustic pulse and generate a casing signal indicative thereof; and means enabled by the casing signal for amplifying said reverberation segment following the initial casing reflection.

22. An acoustic pulse echo apparatus for investigating the quality of the bond between cement and a casing located in a borehole penetrating an earth formation comprising means for generating from inside the casing an acoustic pulse towards a radial segment of the casing and the formation and producing a reflection signal representative of acoustic returns from the interaction of the acoustic pulse with different layers of material in the path of the acoustic pulse, said acoustic pulse being generated with acoustic wave frequencies in a bandwidth selected to stimulate a thickness resonance between the inner and outer walls of the casing and with the acoustic wave frequencies further being selected to render micro-annuli representative of good cement bonds effectively transparent while enhancing reflections from annuli representative of bad cement bonds;

means for selecting a reverberation segment of the reflection signal following an initial casing reflection wherein said reverberation segment is substantially representative of acoustic leakage from reverberations introduced in between the walls of the casing by said acoustic pulse; and means for measuring the energy in the reverberation segment of the reflection signal and produce a bond signal indicative thereof to characterize the quality of the cement bond.

23. The cement bond quality investigating apparatus as claimed in claim 22 wherein said bond signal producing means further includes means for producing a reverberation segment select signal commencing at a time commensurate with the arrival time of the reverberation segment of the reflection signal and continuing for a time commensurate with the duration of the portion of the reflection signal indicative of a bad bond between the casing and the cement; and means controlled by the reverberation segment select signal and coupled to the reflection signal for selecting said reverberation segment from the reflection signal.

24. The cement bond quality investigating apparatus as claimed in claim 23 wherein said bond signal producing means still further includes means for rectifying said selected predetermined segment; and means for integrating said rectified predetermined segment effectively for the duration of said reverberation segment select signal.

25. The apparatus for investigating the quality of the cement bond in accordance with claim 22 wherein said reflection signal producing means is selectively located within the apparatus to establish a predetermined minimum spacing between the casing and the reflection signal producing means to produce a reflection signal with said reverberation segment substantially free from secondary transmission interference.

26. The apparatus for investigating the quality of the cement bond in accordance with claim 25 and further including means responsive to the reflection signal for generating a casing reflection signal representative of a predetermined characteristic of said initial acoustic casing reflection; and means for normalizing said bond signal with the casing reflection signal.

27. The apparatus for investigating the quality of the cement bond in accordance with claim 26 wherein said casing reflection signal generating means further includes means for measuring the amplitude of the casing reflection signal.

28. The apparatus for investigating the quality of the cement bond in accordance with claim 26 wherein said casing reflection signal generating means further includes means for effectively measuring the energy of the casing reflection signal.

29. The apparatus for investigating the quality of the cement bond in accordance with claim 26 wherein the means for generating the casing reflection signal further includes a threshold detector responsive to the reflection signal for sensing a predetermined magnitude indicative of the arrival of said initial acoustic casing reflection and to produce an enabling signal representative thereof; and means responsive to the reflection signal and enabling signal for selecting said casing reflection signal.

30. An acoustic pulse echo apparatus for investigating the quality of the bond between cement and a casing located in a borehole penetrating an earth formation comprising means for generating from inside the casing a highly damped acoustic pulse towards the formation wherein said acoustic pulse has waves at frequencies selected to stimulate a thickness resonance inside the casing walls, said acoustic wave frequencies further being selected to render micro-annuli representative of good cement bonds effectively transparent while enhancing reflections from annuli representative of bad cement bonds; said acoustic pulse generating means being further responsive to acoustic returns produced by said acoustic pulse for producing a reflection signal representative thereof;

said acoustic pulse producing means being at a predetermined minimum spacing from the casing to enable the detection of acoustic reverberations substantially free from secondary transmission interference;

means responsive to said reflection signal for detecting an initial casing reflection from the casing;

means actuated upon the detection of the initial casing reflection signal for selecting a reverberation segment following said initial casing reflection; and means for producing a bond signal indicative of the energy in the selected reverberation segment to characterize the quality of the cement bond.

31. The apparatus for investigating the quality of the cement bond in accordance with claim 30 wherein said predetermined spacing between the casing and the reflection signal producing means is selected sufficiently large to enable the detection of acoustic returns having a magnitude above a predetermined level and substantially attributable to leakage from said reverberations inside the casing walls as a result of said acoustic pulse.

32. The apparatus for investigating the quality of the cement bond in accordance with claim 31 wherein said apparatus has a surface capable of generating secondary transmission interference by reflecting acoustic energy back towards the casing and wherein a predetermined minimum spacing, D, between the casing and said surface is determined in accordance with the relationship $$D > N_r L (C_o/C_1)$$

where L is the thickness of the casing, $C_o$ is the velocity of sound of the material enclosed by the casing, $C_1$ is the velocity of sound inside the casing material and $N_r$ represents a substantial number of reverberations produced within the casing as a result of acoustic energy entrapment from the thickness resonance producing acoustic pulse and is determined by the relationship $$N_r = \frac{\ln (x)}{\ln (|r_o r_1|)}$$

where $r_o$ and $r_1$ are respectively reflection coefficients between the material enclosed by the casing and the casing itself and between the casing and the material adjacent outside of the casing, and where x represents the predetermined level expressed as a fraction of the initial level of the reverberations.

33. An acoustic pulse echo apparatus for investigating the quality of the bond between cement and a casing located in a borehole penetrating an earth formation comprising means for generating from inside the casing an acoustic pulse towards a radial segment of the casing and produce a reflection signal representative of acoustic returns from different layers of material in the path of the acoustic pulse, said acoustic pulse being generated with a bandwidth selected to stimulate a thickness resonance between the inner and outer walls of the casing with substantially reduced reflections from hydraulically secure micro-annuli representative of good bonds and with significantly longer duration reverberations in the casing in the presence of annuli representative of bad cement bonds;

means responsive to the reflection signal for generating a casing reflection signal indicative of the duration of an acoustic reflection from the casing;

means responsive to the casing reflection signal for producing a reverberation segment selection signal to identify a reverberation segment of the reflection signal following the casing reflection;

means enabled by the reverberation segment selection signal for measuring the energy in the reflection signal for the duration of the reverberation segment selection signal and produce a bond signal indicative of the quality of the bond between the casing and the cement located in the path of the acoustic pulse;

means for producing a normalizing signal representative of a predetermined characteristic in the acoustic reflection from the casing; and means for combining said bond signal with the normalizing signal to produce a normalized bond signal representative of the quality of the cement bond.

34. An acoustic pulse echo method of investigating the quality of the bond between cement and a casing located in a borehole penetrating an earth formation comprising the steps of generating a pulse of acoustic energy towards the formation from inside the casing with the acoustic energy having a frequency spectrum which is selected to stimulate the casing into a thickness resonance to trap reverberations in the casing and having said frequency spectrum selected to generate acoustic waves at frequencies whose water wavelengths exceed the thickness of hydraulically secure micro-annuli by a factor sufficient to render said micro-annuli effectively transparent to said acoustic pulse;

deriving a reflection signal representative of acoustic returns from different layers of material in the path of the acoustic pulse; and determining the energy in a reverberation segment of the derived reflection signal to the exclusion of a strong casing reflection in the reflection signal and substantially attributable to acoustic leakage from reverberations inside the casing as an indication of the quality of the bond between the casing and the cement located in the path of the acoustic pulse.

35. The method of investigating the quality of the cement bond in accordance with claim 34 wherein said processing step still further includes the steps of selecting a casing segment of the reflection signal representative of the casing reflection;

producing a casing signal indicative of a predetermined characteristic of the selected casing segment; and applying the casing signal to normalize the determined energy in the reverberation segment relative to said predetermined characteristic of the casing reflection.

36. The method of investigating the quality of the cement bond in accordance with claim 35 wherein said casing signal producing step produces a casing signal effectively representative of the energy in the casing reflection.

37. The method of investigating the quality of the cement bond in accordance with claim 35 wherein said casing signal producing step produces a casing signal effectively representative of an amplitude of the casing reflection.

38. The method of investigating the quality of the cement bond in accordance with claim 34 wherein said detecting step is carried out at a predetermined distance from the casing to provide said reflection signal substantially free from secondary transmission interference.

39. A method for acoustically investigating the quality of the bond between cement and a casing located in a borehole penetrating an earth formation with a pulse echo technique comprising the steps of generating an acoustic pulse inside the casing towards a selected radial segment of the casing and the formation to cause acoustic returns attributable to the acoustic interaction of the acoustic pulse with different layers of material in the path of the acoustic pulse, wherein said acoustic pulse has acoustic wave frequencies in a bandwidth selected to stimulate the casing into a thickness resonance to trap acoustic reverbertions inside the casing walls, with the acoustic wave frequencies further being selected to reduce reflections from micro-annuli representative of good cement bonds while enhancing reflections from annuli representative of bad cement bonds;

detecting the acoustic returns to produce a reflection signal indicative thereof;

selecting a casing segment from the reflection signal representative of a reflection from the casing;

selecting a reverberation segment from the reflection signal representative of reflections occurring subsequent to said casing reflection and substantially representative of leakage returns from reverberations introduced in the casing by the acoustic pulse; and processing said selected segments to cooperatively produce a bond signal indicative of the quality of the cement bond.

40. The method of investigating the quality of the cement bond in accordance with claim 39 wherein said processing step further includes the steps of measuring the energy in said segments; and normalizing the measured energy of the reverberation segment with the measured energy in the casing segment to produce said bond signal.

41. The method for investigating the cement bond in accordance with claim 40 and further comprising the step of preferentially amplifying the selected reverberation segment relative to the casing segment for enhanced accuracy in obtaining a measurement of the quality of the cement bond.

42. An apparatus for acoustically investigating the quality of the bond between cement and a casing located in a borehole penetrating an earth formation with an acoustic pulse echo technique comprising means for producing an acoustic pulse having acoustic wave frequencies selected to stimulate the casing into a thickness resonance with enhanced entrapment of reverberations inside the casing and provide a reflection signal representative of acoustic returns caused by the acoustic pulse;

means for extracting from the reflection signal a frequency segment selected to include casing thickness resonance frequencies and generate a bond signal representative thereof as indicative of the quality of the cement bond;

means for extracting from the reflection signal a reference frequency segment and produce a reference signal indicative thereof; and means for combining the reference signal with the bond signal to provide a normalized bond signal indicative of the quality of the cement bond.

43. The apparatus for investigating the quality of the cement bond as set forth in claim 42 wherein the extracting means includes a pass band filter having its pass band aligned with the casing thickness resonance frequency.

44. The apparatus for investigating the quality of the cement bond as set forth in claim 43 wherein the pass band of the filter has a bandwidth generally less than about 15 per cent of the casing thickness resonance frequency.

45. A method for acoustically evaluating the quality of the bond between cement and a casing in a borehole penetrating an earth formation comprising generating an acoustic pulse from inside the casing towards a radial segment of the casing wherein the acoustic pulse has a frequency bandwidth selected to stimulate a thickness resonance with acoustic reverberations inside the radial segment of the casing;

detecting acoustic returns attributable to the interaction of the acoustic pulse with materials in the path of the acoustic pulse and produce a reflection signal indicative thereof;

selecting a predetermined frequency band from the reflection signal wherein the selected frequency band includes casing thickness resonance frequencies and produce a bond signal representative thereof to indicate the quality of the cement bond;

selecting a reference frequency band from the reflection signal and produce a reference signal indicative thereof; and combining the reference signal with the bond signal for normalization thereof.

46. The method for evaluating the quality of the cement bond as claimed in claim 45 wherein the step of selecting the predetermined frequency band selects a band of signals over a frequency range of generally less than about 15 percent of the casing thickness resonance frequency.

47. An apparatus for acoustically investigating the quality of the bond between cement and a casing located in a borehole penetrating an earth formation comprising a tool sized to vertically move inside the casing with a clearance between the tool and the casing; and a plurality of radially-directive acoustic transducers peripherally mounted around the tool to operatively direct acoustic pulses through fluid in the clearance between the tool and the casing and in a radial direction towards the formation for circumferential and longitudinal investigation of the cement bond, said transducers being each so circumferentially spaced and selected to provide an acoustic pulse directed at a different radial segment of the formation and having a frequency bandwidth selected to stimulate a thickness resonance in between the inner and outer casing walls and produce a reflection signal in response to acoustic returns attributable to the interaction of the acoustic pulse with different materials in the path of the acoustic pulse.

48. The apparatus for investigating the quality of the cement bond as claimed in claim 47 wherein the transducers are selectively radially mounted on the tool to establish a predetermined radial spacing from the casing to reduce secondary transmission interference in said reflection signal.

49. The apparatus for investigating the quality of the cement bond as claimed in claim 47 and further including means for energizing the transducers; and means for measuring the time period between each transducer energization and detection of an acoustic return thereby to determine the position of the transducers relative to the casing.

50. The apparatus for investigating the quality of the cement bond as claimed in claim 47 and further including means for sequentially energizing the transducers;

means for amplifying the reflection signals from the transducers with a common amplifier;

means for producing control signals representative of the amplitude of the reflections signals from the transducers; and means for adjusting the gain of the amplifying means with the control signal associated with the transducer whose reflection signal is being amplified.

51. An apparatus for acoustically investigating a borehole penetrating an earth formation comprising a tool sized to move inside the borehole with a clearance between the tool and the borehole; and a plurality of radially directive acoustic transducers peripherally mounted on and around the tool to operatively direct acoustic pulses through the clearance between the tool and the borehole towards different radial segments of the formation in correspondence with the peripheral locations of the acoustic transducers for investigation of the borehole, said transducers being each selected to provide an acoustic pulse having a frequency bandwidth selected to stimulate reflections from said radial segments, with each transducer producing a reflection signal in response to the interaction of its acoustic pulse with a radial segment of the borehole wall in the path of the acoustic pulse.

52. An apparatus for investigating with an acoustic pulse a casing located in a borehole penetrating an earth formation comprising means for directing an acoustic pulse from inside the casing in a radial direction at a radial segment of the inner wall of the casing, wherein the acoustic pulse has acoustic wave frequencies selected to stimulate a thickness resonance inside the radial segment with enhanced entrapment of reverberations and providing a reflection signal representative of acoustic returns caused by the acoustic pulse;

means for selecting from the reflection signal a portion which includes acoustic returns attributable to the acoustic reverberations inside the casing walls;

means for generating a spectrum signal representative of the frequency spectrum of the selected portion; and means for determining the frequency of components in said spectrum signal contributing to a peak value thereof and producing a thickness signal representative thereof as the casing thickness.

53. The apparatus for investigating a casing as claimed in claim 52 wherein said means for determining the peak value further includes means for producing samples of the spectrum signal with associated values of the frequency of the samples;

means for scanning said spectrum samples for a peak value thereof and selecting the associated frequency value as an indication of the thickness of the casing.

54. The apparatus for investigating a casing as claimed in claim 53 wherein said portion selection means further includes means responsive to the reflection signal for detecting a signal therein representative of an initial acoustic reflection signal from the casing; and means responsive to the detected casing reflection signal for selecting said portion following the initial casing reflection.

55. A method for acoustically investigating a casing cemented in a borehole penetrating an earth formation comprising the steps of generating an acoustic pulse from inside the casing in a radial direction towards the formation wherein the acoustic pulse has a frequency bandwidth selected to stimulate a thickness resonance with acoustic reverberations inside the walls of a radial segment of the casing;

detecting acoustic returns arising from the interaction of the acoustic pulse with materials in the path of the acoustic pulse and producing a reflection signal indicative thereof;

selecting from the reflection signal a portion which includes acoustic returns produced by said acoustic reverberations inside the walls of the casing;

forming a frequency spectrum of the selection portion; and determining the frequency of components which contribute to a maximum peak in the frequency spectrum of the selected portion and producing a signal representative thereof as an indication of the casing thickness.

56. The method of acoustically investigating the casing in a borehole as claimed in claim 55 wherein said frequency determining step further includes the steps of digitizing the frequency spectrum to form samples thereof with associated frequency values for the samples;

scanning the samples to determine a peak value thereof; and recording the frequency value of the peak value of the samples as an indication of the thickness of the casing.

57. The method of acoustically investigating a borehole as claimed in claim 55 wherein said frequency spectrum forming step further includes the steps of applying said selected portion to a spectrum analyzer to generate an amplitude signal representative of the amplitude of the frequency components in the selected portion and a frequency signal representative of the frequency of the components in said amplitude signal;

storing said amplitude and frequency signals;

scanning said stored amplitude and frequency signals to detect a peak value of the amplitude signal with its associated frequency signal as an indication of the thickness of the casing.

58. The method of acoustically investigating a borehole as claimed in claim 55 wherein said frequency spectrum forming step further includes the steps of digitizing said selected portion to form digital samples thereof, and forming a fourier transform of the digital samples of the selected portion.

59. The method of acoustically investigating a borehole as claimed in claim 58 and further including the step of increasing the amplitude of the selected portion of the reflection signal prior to said digitizing step.

60. An apparatus for investigating with an acoustic pulse a casing cemented in a borehoele penetrating an earth formation comprising means for generating a highly damped acoustic pulse from inside the casing in a radial direction towards a radial segment of the casing with said acoustic pulse being generated with acoustic wave frequencies in a bandwidth selected to stimulate an acoustic resonance between the walls of the casing with acoustic reverberations and providing a reflection signal representative of acoustic returns caused by the acoustic pulse;

means for generating digital samples of the reflection signal;

means for selecting samples representative of said casing reverberations and occurring subsequent to samples representative of an initial casing reflection;

means for generating a spectrum of the selected reverberation samples and form amplitude samples with associated frequency values; and means for determining a maximum amplitude sample and its associated frequency value as an indication of the thickness of the casing.

61. The apparatus for investigating a casing as claimed in claim 60 and further including means for summing the absolute value of the selected samples representative of the reverberations in the casing as a measurement of the quality of the bond between the casing and cement.

62. The apparatus for investigating a casing as in claim 60 and further including means for selecting samples representative of an initial acoustic casing reflection of the inner wall of the casing;

means for summing the absolute values of the samples representative of the initial acoustic casing reflection;

means for summing the absolute values of the selected samples representative of the casing reverberations as a measurement of the quality of the bond between the casing and cement; and means for forming a quotient between the respective sums generated by the summing means to normalize said measurement of the quality of the cement bond.

63. A method for investigating a casing cemented in a borehole penetrating an earth formation comprising the steps of generating a highly damped acoustic pulse from inside the casing in a radial direction towards a radial segment of the casing with said acoustic pulse being generated with acoustic wave frequencies in a bandwidth selected to stimulate the casing into a thickness resonance with acoustic reverberations between the walls of the casing;

detecting acoustic returns arising from the interaction of the acoustic pulse with materials in the path of the acoustic pulse and producing a reflection signal indicative thereof;

converting the reflection signal to digital samples;

forming a frequency spectrum of samples representative of casing reverberations occurring subsequent to samples representative of an initial acoustic reflection off the inner wall of the casing with the frequency spectrum composed of amplitude samples with associated frequency values;

determining a peak amplitude sample in the frequency spectrum; and recording a thickness signal representative of the associated frequency value of the peak amplitude sample as an indication of casing thickness.

64. The method for investigating a casing as claimed in claim 63 and further including summing absolute values of samples representative of casing reverberations to provide a bond signal indicative of the quality of the bond between the casing and the cement.

65. The method for investigating a casing as claimed in claim 64 and further including summing absolute values of samples representative of the initial casing reflection; and forming a quotient between said respectively summed samples to provide a normalized bond signal.

66. An apparatus for evaluating the cement bond of a casing cemented in a borehole penetrating an earth formation from a reflection signal derived from an acoustic investigation of the casing with an acoustic pulse directed at a radial segment of the casing and formed of acoustic waves at frequencies selected to stimulate a thickness resonance inside the casing walls comprising means for selecting from the reflection signal a reverberation segment substantially representative of acoustic reverberations between the casing walls at said radial segment;

means for determining the energy in the selected reverberation segment and producing a bond signal indicative thereof to characterize the quality of the cement bond behind the casing;

means for determining from a reverberation segment a casing thickness signal representative of the thickness of the casing at said radial segment; and means for normalizing said bond signal with said casing thickness signal to substantially remove the effect of casing thickness variations from the characterization of the quality of the cement bond at said radial segment.

67. The apparatus for evaluating the cement bond as claimed in claim 66 wherein said bond signal producing means further includes means for determining the energy in a casing segment of the reflection signal representative of an acoustic reflection off an inner wall of the casing and provide a casing signal indicative thereof; and means for normalizing said bond signal with said casing signal to provide a characterization of the quality of the cement bond at said radial segment and corrected for borehole conditions and casing thickness.

68. A method for evaluating the cement bond of a casing cemented in a borehole penetrating an earth formation from a reflection signal derived from an acoustic investigation of the casing with an acoustic pulse directed at a radial segment of the casing and formed of acoustic waves at frequencies selected to stimulate a thickness resonance inside the casing walls comprising the steps of deriving from the reflection signal a reverberation segment substantially representative of acoustic reverberations between the casing walls at said radial segment;

measuring the energy in the selected reverberation segment and provide a bond signal indicative thereof to characterize the quality of the cement bond behind said radial segment;

measuring the thickness of the casing effectively at said radial segment and provide a thickness signal indicative thereof; and effectively removing from said bond signal with said thickness signal, variations, which are substantially attributable to casing thickness changes.

69. The method for evaluating the cement bond of a casing cemented in a borehole as claimed in claim 68 wherein said step for removing variations attributable to casing thickness changes comprises dividing the bond signal by the thickness signal.

70. The method for evaluating the cement bond of a casing cemented in a borehole as claimed in claim 69 wherein the bond signal producing step further includes the steps of measuring the magnitude of a casing reflection segment in the reflection signal; and normalizing the bond signal with the measured magnitude of the casing reflection to provide a bond signal which characterizes the cement bond quality substantially independent of borehole conditions and casing thickness.

* * * * *